US 6,526,778 B2

(12) United States Patent
Zollinger et al.

(10) Patent No.: US 6,526,778 B2
(45) Date of Patent: Mar. 4, 2003

(54) RESILIENT CONTAINERS FOR HYPERPOLARIZED GASES AND ASSOCIATED METHODS

(75) Inventors: David L. Zollinger, Chapel Hill, NC (US); Daniel M. Deaton, Raleigh, NC (US); Bastiaan Driehuys, Durham, NC (US); Kenton C. Hasson, Durham, NC (US)

(73) Assignee: Medi-Physics, Inc., Princeton, NJ (US)

( * ) Notice: Subject to any disclaimer, the term of this patent is extended or adjusted under 35 U.S.C. 154(b) by 0 days.

(21) Appl. No.: 10/153,197

(22) Filed: May 22, 2002

(65) Prior Publication Data

US 2003/0009126 A1 Jan. 9, 2003

Related U.S. Application Data

(62) Division of application No. 09/334,400, filed on Jun. 16, 1999, now Pat. No. 6,423,387.
(60) Provisional application No. 60/089,692, filed on Jun. 17, 1998.

(51) Int. Cl.[7] .................................................. F25J 3/00
(52) U.S. Cl. ........................................ 62/640; 62/45.1
(58) Field of Search ...................... 62/640, 45.1, 919; 628/204.8

(56) References Cited

U.S. PATENT DOCUMENTS

| 3,657,363 A | 4/1972 | Dorko ........................ 260/642 |
| 3,748,864 A | 7/1973 | Lofredo et al. ................ 62/22 |
| 3,966,781 A | 6/1976 | Atkinson et al. ..... 260/410.9 R |
| 4,080,429 A | 3/1978 | Koeppe et al. ............. 423/262 |

(List continued on next page.)

FOREIGN PATENT DOCUMENTS

| GB | 2091884 | 4/1982 |
| WO | PCT/US97/05004 | 3/1997 |
| WO | PCT/US97/05084 | 3/1997 |
| WO | WO 97/37239 | 10/1997 |
| WO | WO 99/07415 | 2/1999 |
| WO | WO 99/08941 | 2/1999 |
| WO | WO 99/14582 | 2/1999 |
| WO | PCT/US97/05166 | 3/1999 |
| WO | WO 99/17304 | 4/1999 |
| WO | WO 99/25243 | 5/1999 |
| WO | WO 00/21601 | 4/2002 |

OTHER PUBLICATIONS

Albert et al., "$^{129}$Xe Relaxation Catalysis by Oxygen", Abstracts of the 11th Annual Meetings of the Society for Magnetic Resonance Medicine, (1992).

(List continued on next page.)

Primary Examiner—Ronald Capossela
(74) Attorney, Agent, or Firm—Myers Bigel Sibley & Sajovec PA

(57) ABSTRACT

A resilient multi-layer container is configured to receive a quantity of hyperpolarized noble fluid such as gas and includes a wall with at least two layers, a first layer with a surface which minimizes contact-induced spin-relaxation and a first or second layer which is substantially impermeable to oxygen. The container is especially suitable for collecting and transporting $^3$He. The resilient container can be formed of material layers which are concurrently responsive to pressure such as polymers, deuterated polymers, or metallic films. The container can include a capillary stem and/or a port or valve isolation means to inhibit the flow of gas from the main volume of the container during transport. The resilient container can be configured to directly deliver the hyperpolarized noble gas to a target interface by deflating or collapsing the inflated resilient container. In addition, single layer resilient containers with $T_1$'s of above 4 hours for $^{129}$Xe and above 6 hours for $^3$He include materials with selected relaxivity values. In addition, a bag with a port fitting or valve member and one or more of a capillary stem and port isolation means is configured to minimize the depolarizing effect of the container valve or fitting(s). Also disclosed is a method for determining the gas solubility in an unknown polymer or liquid using the measured relaxation time of a hyperpolarized gas.

33 Claims, 14 Drawing Sheets

U.S. PATENT DOCUMENTS

| | | |
|---|---|---|
| 4,369,048 A | 1/1983 | Pence .......................... 55/66 |
| 4,417,909 A | 11/1983 | Weltmer, Jr. ................... 62/12 |
| 4,586,511 A | 5/1986 | Clark, Jr. ..................... 128/653 |
| 4,599,462 A | 7/1986 | Michl ......................... 568/702 |
| 4,755,201 A | 7/1988 | Eschwey et al. ............... 62/12 |
| 4,914,160 A | 4/1990 | Azizian .................... 525/329.3 |
| 4,977,749 A | 12/1990 | Sercel ........................ 62/51.1 |
| 5,007,243 A | 4/1991 | Yamaguchi et al. ......... 62/51.1 |
| 5,039,500 A | 8/1991 | Shino et al. ................ 423/262 |
| 5,161,382 A | 11/1992 | Missimer .................... 62/46.1 |
| 5,545,396 A | 8/1996 | Albert et al. ................. 424/93 |
| 5,612,103 A | 3/1997 | Driehuys et al. .......... 428/34.7 |
| 5,617,860 A | 4/1997 | Chupp et al. ............ 128/653.4 |
| 5,642,625 A | 7/1997 | Cates, Jr. et al. ............ 62/55.5 |
| 5,809,801 A | 9/1998 | Cates, Jr. et al. ............. 62/637 |
| 6,128,918 A | 10/2000 | Deaton et al. ................ 62/610 |

OTHER PUBLICATIONS

Albert et al., "Relaxation of $^{129}$Xe in Model Biological Systems: On Probing the Mechanism of General Anesthesia", Abstracts of the 11th Annual Meetings of the Society for Magnetic Resonance Medicine, (1992).

Becker et al., "Study Of Mechanical Compression Of Spin–Polarized $^3$He Gas", Nuclear Instruments And Methods In Physics Research, vol. A 346, pp. 45–51 (1994).

Bhaskar et al., "Efficiency of Spin Exchange between Rubidium Spins and $^{129}$Xe Nuclei in a Gas", *Physical Review Letters*, vol. 49, pp. 25–28 (1982).

Brochure, Jensen Inert Products, Gas Sampling Bags, jensen@jenseninert.com (Copyright 1997).

Cain et al., "Nuclear Spin Relation Mechanisms and Mobility of Gases in Polymers", 94 J. Phys. Chem. No. 5, pp. 2128–2135 (1990).

Cates et al., "Laser Production of Large Nuclear–Spin Polarization in Frozen Xenon", Phys. Rev. Lett., vol. 65, No. 20, pp. 2591–2594 (1990).

Cates et al., "Rb–$^{129}$Xe spin–exchange rates due to binary and three–body collisions at High Xe pressures", Physical Review A, vol. 45, pp. 4631–4639 (1992).

Cummings et al., "Optical pumping of Rb vapor using high–power $Ga_{1-x}A_x$ As diode laser arrays", Phys. Rev. A, vol. 51, No. 6, pp. 4842–4851 (1995).

De Schepper, "The HERMES $^3$He target," AIP Conf. Proc., vol. 421, No. 1, pp. 16–25 (1/98).

Driehuys et al., "High–volume production of laser–polarized $^{129}$Xe", 69 App. Phys. Lett. (12), pp. 1668–1670 (1996).

Driehuys et al., "Surface Relaxation Mechanisms of Laser–Polarized $^{129}$Xe", 74 Phys. Rev. Lett., No. 24, pp. 4943–4946 (1995).

Freed, "Dynamic effects of pair correlation functions on spin relaxation by translational diffusion in liquids. II. Finite jumps and independent $T_1$ processes", 68 J. Chem. Phys. vol. 9, pp. 4034–4037 (1978).

Gao, J.H. et al., "Magnetization and Diffusion Effects in NMR Imaging of Hyperpolarized Substances," Magn. Reson. Med., vol. 37, No. 1, pp. 153–158 (Jan. 1997).

Gatzke et al., "Extraordinarily Slow Nuclear Spin Relaxation in Frozen Lazer–Polarized $^{129}$Xe", Phys. Rev. Lett., vol. 70, No. 5, pp. 690–693 (1993).

Gregory et al., "Pore–structure determinations of silica aerogels by $^{129}$Xe NMR spectroscopy and imaging," J. of Mag. Res., vol. 131, pp. 327–335 (1998).

Happer et al., "An Optical Pumping Primer", Hyperfine Interactions 38, pp. 435–470 (1987).

Heil et al., "Very long nuclear relaxation times of spin polarized helium 3 in metal coated cells", Physics Letters A 201, pp. 337–343 (1995).

Hunt et al., "Nuclear Magnetic Resonance of $^{129}$Xe in Natural Xenon", 130 Phys Rev. pp. 2302–2305 (1963).

Hwang et al., "Dynamic effects of pair correlation functions on spin relaxation by translational diffusion in liquids", 63 J. Chem. Phys. No. 9, pp. 4017–4025 (1975).

Kaatz, P. et al., "A comparison of molecular hyperpolarizabilities from gas and liquid phase measurements," J. Chem. Phys. vol. 108, No. 3, pp. 849–856 (Jan. 15, 1998).

Kauczor, U. et al., "The helium–3 MRT of pulmonary ventilation; the initial clinical applications," Abstract, Rofo Fortschr Geb Rontgenstru Neuen Bildegeb Verfahr, vol. 166, No. 3 (Mar. 1997).

Kauczor, H. et al., "MRI using hyperpolarized noble gases," Abstract, Eur. Radiol., vol. 8, No. 5 1998).

Laloë, F. et al., "Workshop on Polarized $^3$He Beams and Targets", AIP Conference Proceedings #131 (1984).

Mansfeld et al., "The use of $^{129}$Xe NMR exchange spectroscopy for probing the microstructure of porous materials," Chem. Phys. Ltrs., vol. 213, No. 1,2, pp. 153–157 (Oct. 1, 1993).

Middleton et al., "MR Imaging With Hyperpolarized $^3$He Gas", Magnetic Resonance In Medicine, vol. 33, pp. 271–275 (1995).

Middleton, "The Spin Structure of The Neutron Determined Using A Polarized $^3$He Target", Ph.D. Dissertation, Princeton University (1994).

Miller et al., "Xenon NMR: Chemical shifts of a general anesthetic common solvents, proteins, and membranes", Proc. of the Nat. Academy of Science (USA), vol. 78, No. 8, pp. 4946–4949 (1981).

Mugler et al., "MR Imaging and Spectroscopy Using Hyperpolarized $^{129}$Xe Gas: Preliminary Human Results", Magnetic Resonance in Medicine, vol. 37, pp. 809–815 (1997).

Nacher, P.J. et al., "Recent results on hyperpolarized $^3$He–$^4$He liquid mixtures," vol. 46, Supp. Pt. S6, pp. 3025–3032 (1966).

Newbury et al., "Gaseous $^3$He–$^3$He magnetic dipolar spin relaxation", 48 Phys. Rev. A., No. 6, pp. 4411–4420 (1993).

Pasquier et al., "$^{129}$Xe NMR as a probe of the dynamics of gas confined in porus Vycor," Mag. Res. Imaging, vol. 14, No. 7/8, pp. 971–973 (1996).

Patyal et al., "Longitudinal Relaxation and Diffusion Measurements Using Magnetic Resonance Signals from Laser–Hyperpolarized $^{129}$Xe Nuclei," J. Magn. Reson., vol. 126, pp. 58–65 (May 1997).

Pauly, "Permeability and Diffusion Data," The Polymer Handbook, VI/435–449.

Pfeffer et al., "$^{129}$Xe Gas NMR Spectroscopy and Imaging with a Whole–Body Imager," J. Mag. Res., Series A, 108, pp. 106–109 (1994).

Pietraβ, Tanja, et al., *Optically Polarized $^{129}$Xe in NMR Spectroscopy, Advanced Materials*, vol. 10, pp. 826–838 (1995).

Raftery et al., "NMR of optically pumped xenon thin films", Chem. Phys. Lett., vol. 191, pp. 385–390 (1992).

Reif, "Fundamentals of Statistical and Thermal Physics", McGraw–Hill, Ch. 12–14, pp 461–493 (1965).

Saam et al., "Nuclear relaxation of $^3$He in the presence of $O_2$", Phys. Rev. A, 52, pp. 862–865 (1995).

Sauer et al., "Laser–Polarized Liquid Xenon", Chem. Phys. Lett., vol. 277, pp. 153–158 (1997).

Schearer, Optical Pumping of Neon $^3P_2$ Metastable Atoms, Phys Rev., 180:83 (1969).

Song, Y.Q. et al., "Effects of diffusion on magnetic resonance imaging of laser–polarized xenon gas," J. Chem. Phys., vol. 108, No. 15, pp. 6233–6239 (Apr. 15, 1998).

Zeng et al., "Experimental determination of the rate constants for spin exchange between optically pumped K, Rb, and Cs atoms and $^{129}$Xe nuclei in alkali–metal—noble–gas van der Waals molecules", Physical Review A, vol. 31, pp. 260–278 (1985).

PCT International Search Report, PCT International Application No. PCT/US 99/13597, mailed Sep. 3, 2000.

EXPERIMENTAL RESULTS

| | MATERIAL | DATE | $T_{1c}$ min | ERROR $T_{1c}$ min | $T_{1p}$ min | ERROR $T_{1p}$ min | RELAXIVITY cm/min | ERROR RELAXIVITY cm/min | $T_1^{cc}$ min | ERROR $T_1^{cc}$ min |
|---|---|---|---|---|---|---|---|---|---|---|
| XENON | POLYETHYLENE (LDPE) | 11.18.97 | 102 | 7.32 | 31.7 | 1.23 | 0.0370 | 0.00391 | 5.59 | 0.59 |
| | POLYETHYLENE (HDPE) | 11.18.97 | 113 | 4.96 | 33.2 | 2.18 | 0.0362 | 0.00246 | 5.71 | 0.39 |
| | POLYPROPYLENE (PP) | 11.20.97 | 123 | 6.18 | 25.1 | 1.35 | 0.0540 | 0.00349 | 3.83 | 0.25 |
| | POLYTETRAFLUOROETHYLENE (PTFE) | 11.25.97 | 107 | 3.67 | 41.7 | 2.12 | 0.0249 | 0.00162 | 8.30 | 0.54 |
| | POLYAMIDE - NYLON 6 | 11.25.97 | 118 | 6.96 | 68.6 | 2.55 | 0.0104 | 0.00156 | 19.91 | 2.99 |
| | SILICONE ELASTOMER | 12.17.97 | 118 | 2.58 | 5.23 | 0.299 | 0.3112 | 0.00717 | 0.67 | 0.02 |
| | POLYIMIDE (PI) | 12.18.97 | 126 | 5.98 | 49.1 | 1.33 | 0.0212 | 0.00169 | 9.78 | 0.78 |
| HELIUM | POLYETHYLENE (LDPE) | 3.31.98 | 700 | 28.1 | 470 | 5.16 | 0.0012 | 0.00015 | 170.80 | 21.22 |
| | POLYETHYLENE (HDPE) | 5.10.98 | 681 | 45.98 | 213.4 | 2.9 | 0.0056 | 0.00055 | 37.11 | 3.66 |
| | POLYPROPYLENE (PP) | 5.4.98 | 681 | 45.98 | 75.2 | 0.5 | 0.0205 | 0.00156 | 10.09 | 0.77 |
| | POLYTETRAFLUOROETHYLENE (PTFE) | 4.3.98 | 700 | 28.1 | 98.7 | 3.28 | 0.0151 | 0.00071 | 13.72 | 0.65 |
| | POLYAMIDE - NYLON 6 | 5.11.98 | 681 | 45.98 | 342.3 | 2.3 | 0.0025 | 0.00034 | 82.18 | 11.17 |
| | SILICONE ELASTOMER | 3.18.98 | 700 | 28.1 | 41.1 | 1.01 | 0.0397 | 0.00169 | 5.21 | 0.22 |
| | POLYIMIDE (PI) | 5.10.98 | 681 | 45.98 | 217.1 | 2.7 | 0.0054 | 0.00054 | 38.05 | 3.78 |

FIG. 5.

PREDICTED RESULTS

| MATERIAL | S (MEASURED) | S (LITERATURE) | [1H] mol/L | D cm²/s | $T_{1\rho}$ s | RELAXIVITY cm/min | $T_1^{cc}$ min | LENGTH/SCALE μm |
|---|---|---|---|---|---|---|---|---|
| XENON | | | | | | | | |
| POLYETHYLENE (LDPE) | 0.683 | 0.5896 | 131.43 | 6.90E-08 | 0.065 | 0.0421 | 4.91 | 0.67 |
| POLYETHYLENE (HDPE) | 0.424 | - | 135.71 | - | - | 0.0266 | 7.79 | - |
| POLYPROPYLENE (PP) | 0.682 | - | 128.57 | - | - | 0.0416 | 4.98 | - |
| POLYTETRAFLUOROETHYLENE (PTFE) | 0.726 | 0.7496 | 88.00 | 4.00E-09 | 0.006 | 0.0366 | 5.65 | 0.05 |
| POLYAMIDE - NYLON 6 | 0.310 | - | 98.74 | - | - | 0.0166 | 12.49 | - |
| SILICONE ELASTOMER | 1.930 | 3.9912 | 105.41 | 4.80E-06 | 5.666 | 0.1066 | 1.94 | 52.15 |
| POLYIMIDE (PI) | 4.200 | - | 37.17 | - | - | 0.1377 | 1.50 | - |
| HELIUM | | | | | | | | |
| POLYETHYLENE (LDPE) | 0.0069 | 0.0055 | 131.43 | 6.80E-06 | 0.601 | 0.0014 | 148.68 | 20.22 |
| POLYETHYLENE (HDPE) | 0.0035 | 0.0028 | 135.71 | 3.07E-06 | 0.263 | 0.0007 | 288.45 | 8.98 |
| POLYPROPYLENE (PP) | 0.0130 | 0.0001 | 128.57 | 1.95E-05 | 1.763 | 0.0026 | 79.79 | 58.63 |
| POLYTETRAFLUOROETHYLENE (PTFE) | 0.0190 | 0.1104 | 88.00 | 8.11E-07 | 0.126 | 0.0029 | 71.57 | 3.20 |
| POLYAMIDE - NYLON 6 | 0.0030 | 0.0043 | 98.74 | - | - | 0.0005 | 394.53 | - |
| SILICONE ELASTOMER | 0.0340 | 0.0430 | 105.41 | 4.10E-05 | 4.521 | 0.0061 | 33.69 | 136.14 |
| POLYIMIDE (PI) | 0.0310 | - | 37.17 | - | - | 0.0033 | 62.23 | - |

FIG. 6.

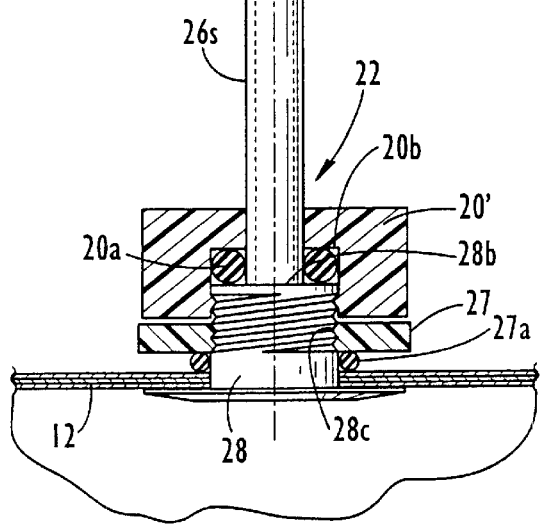
FIG. 9.
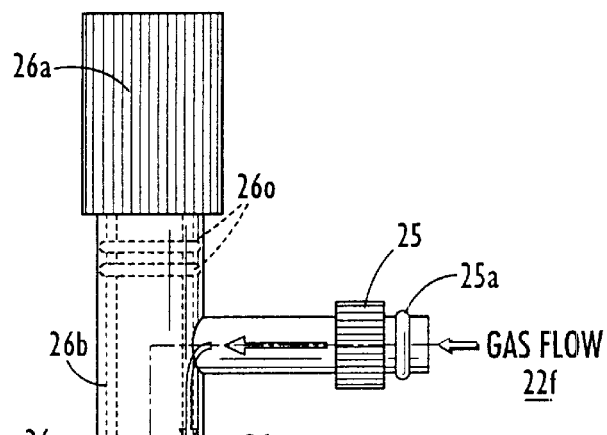
FIG. 10.
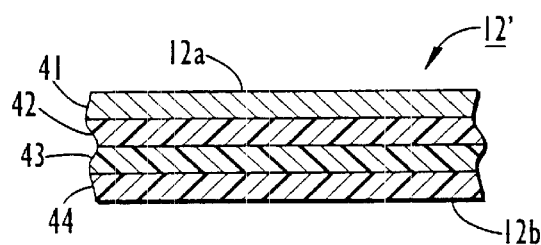
FIG. 11.
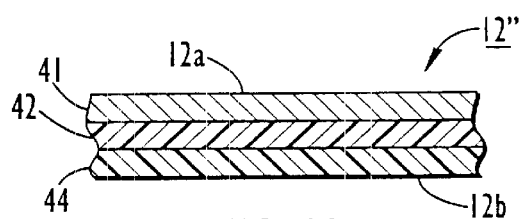
FIG. 12.
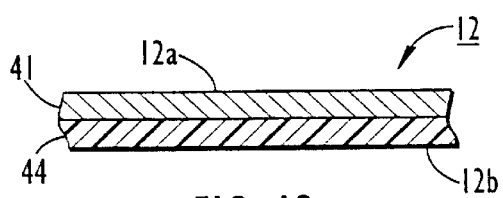

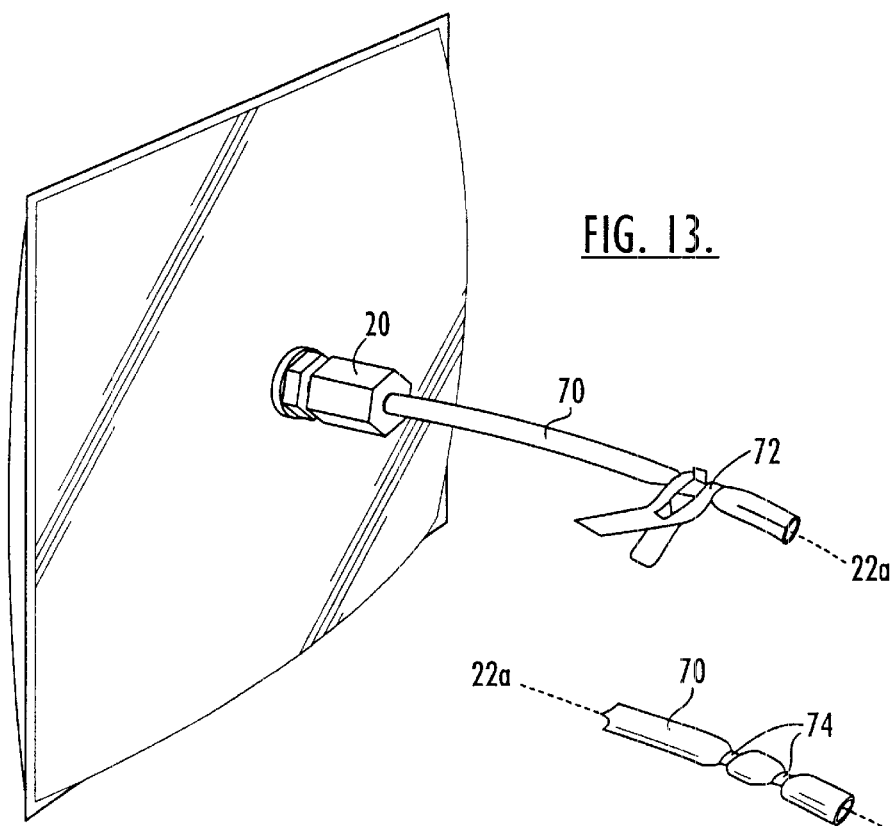
FIG. 13.
FIG. 14.
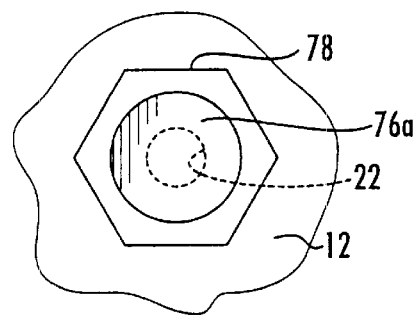
FIG. 15.
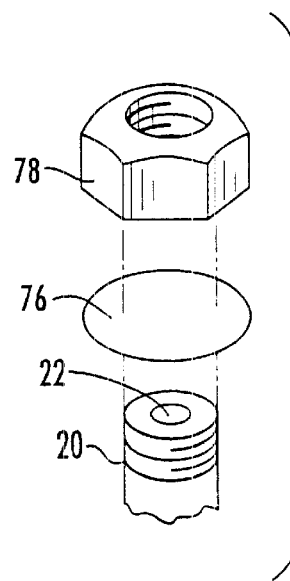
FIG. 15A.

RESILIENT CONTAINERS FOR HYPERPOLARIZED GASES AND ASSOCIATED METHODS

RELATED APPLICATIONS

This application is a divisional of U.S. patent application Ser. No. 09/334,400, filed Jun. 16, 1999 now U.S. Pat. No. 6,423,387, which claims priority from U.S. Provisional Application No. 60/089,692 filed on Jun. 17, 1998. This application is also related to issued U.S. Pat. No. 6,128,918 filed on Jul. 30, 1998. The contents of these documents are incorporated by reference as if recited in full herein.

This invention was made with Government support under AFOSR Grant No. F41624-97-C-9001 and NIH Grant No. 1 R43 HL59022-01. The United States Government has certain rights in this invention.

FIELD OF THE INVENTION

The present invention relates to processing, storage, transport and delivery containers for hyperpolarized noble gases.

BACKGROUND OF THE INVENTION

Conventionally, Magnetic Resonance Imaging ("MRI") has been used to produce images by exciting the nuclei of hydrogen molecules (present in water protons) in the human body. However, it has recently been discovered that polarized noble gases can produce improved images of certain areas and regions of the body which have heretofore produced less than satisfactory images in this modality. Polarized Helium-3 ("$^3$He") and Xenon-129 ("$^{129}$Xe") have been found to be particularly suited for this purpose. Unfortunately, as will be discussed further below, the polarized state of the gases are sensitive to handling and environmental conditions and, undesirably, can decay from the polarized state relatively quickly.

Hyperpolarizers are used to produce and accumulate polarized noble gases. Hyperpolarizers artificially enhance the polarization of certain noble gas nuclei (such as $^{129}$Xe or $^3$He) over the natural or equilibrium levels, i.e., the Boltzmann polarization. Such an increase is desirable because it enhances and increases the MRI signal intensity, allowing physicians to obtain better images of the substance in the body. See U.S. Pat. No. 5,545,396 to Albert et al., the disclosure of which is hereby incorporated herein by reference as if recited in full herein.

In order to produce the hyperpolarized gas, the noble gas is typically blended with optically pumped alkali metal vapors such as rubidium ("Rb"). These optically pumped metal vapors collide with the nuclei of the noble gas and hyperpolarize the noble gas through a phenomenon known as "spin-exchange". The "optical pumping" of the alkali metal vapor is produced by irradiating the alkali-metal vapor with circularly polarized light at the wavelength of the first principal resonance for the alkali metal (e.g., 795 nm for Rb). Generally stated, the ground state atoms become excited, then subsequently decay back to the ground state. Under a modest magnetic field (10 Gauss), the cycling of atoms between the ground and excited states can yield nearly 100% polarization of the atoms in a few microseconds. This polarization is generally carried by the lone valence electron characteristics of the alkali metal. In the presence of non-zero nuclear spin noble gases, the alkali-metal vapor atoms can collide with the noble gas atoms in a manner in which the polarization of the valence electrons is transferred to the noble-gas nuclei through a mutual spin flip "spin-exchange".

After the spin-exchange has been completed, the hyperpolarized gas is separated from the alkali metal prior to introduction into a patient to form a non-toxic or sterile composition. Unfortunately, during and after collection, the hyperpolarized gas can deteriorate or decay (lose its hyperpolarized state) relatively quickly and therefore must be handled, collected, transported, and stored carefully. The "$T_1$" decay constant associated with the hyperpolarized gas's longitudinal relaxation time is often used to describe the length of time it takes a gas sample to depolarize in a given container. The handling of the hyperpolarized gas is critical, because of the sensitivity of the hyperpolarized state to environmental and handling factors and the potential for undesirable decay of the gas from its hyperpolarized state prior to the planned end use, i.e., delivery to a patient. Processing, transporting, and storing the hyperpolarized gases—as well as delivery of the gas to the patient or end user—can expose the hyperpolarized gases to various relaxation mechanisms such as magnetic gradients, ambient and contact impurities, and the like.

Typically, hyperpolarized gases such as $^{129}$Xe and $^3$He have been collected in relatively pristine environments and transported in specialty glass containers such as rigid Pyrex™ containers. However, to extract the majority of the gas from these rigid containers, complex gas extraction means are typically necessary. Hyperpolarized gas such as $^3$He and $^{129}$Xe has also been temporarily stored in single layer resilient Tedlar® and Teflon® bags. However, these containers have produced relatively short relaxation times.

One way of inhibiting the decay of the hyperpolarized state is presented in U.S. Pat. No. 5,612,103 to Driehuys et al. entitled "Coatings for Production of Hyperpolarized Noble Gases." Generally stated, this patent describes the use of a modified polymer as a surface coating on physical systems (such as a Pyrex™ container) which contact the hyperpolarized gas to inhibit the decaying effect of the surface of the collection chamber or storage unit.

However, there remains a need to address and reduce dominant and sub-dominant relaxation mechanisms and to decrease the complexity of physical systems required to deliver the hyperpolarized gas to the desired subject. Minimizing the effect of one or more of these factors can increase the life of the product by increasing the duration of the hyperpolarized state. Such an increase is desired so that the hyperpolarized product can retain sufficient polarization to allow effective imaging at delivery when transported over longer transport distances and/or stored for longer time periods from the initial polarization than has been viable previously.

OBJECTS AND SUMMARY OF THE INVENTION

In view of the foregoing, it is an object of the present invention to process and collect hyperpolarized gas in improved resilient containers which are configured to inhibit depolarization in the collected polarized gas and to provide a longer $T_1$ for $^3$He and $^{129}$Xe than has been achieved in the past.

It is another object of the present invention to provide an improved container which can be configured to act as both a transport container and a delivery mechanism to reduce the amount of handling or physical interaction required to deliver the hyperpolarized gas to a subject.

It is a further object of the present invention to provide an improved, relatively non-complex and economical container which can prolong the polarization life of the gas in a container and reduce the amount of polarization lost during storage, transport, and delivery.

It is yet another object of the invention to provide methods, surface materials and containers which will minimize the depolarizing effects of the hyperpolarized state of the gas (especially $^3$He) attributed to one or more of paramagnetic impurities, oxygen exposure, and surface relaxation.

It is an additional object of the present invention to provide a method to determine the gas solubility in polymers or liquids with respect to hyperpolarized $^{129}$Xe or $^3$He.

These and other objects are satisfied by the present invention which is directed to resilient containers which are configured to reduce surface or contact-induced depolarization by forming an inner contact surface of a first material (of a predetermined thickness) which acts to minimize the associated surface or contact depolarization. In particular, a first aspect of the invention is directed to a container for receiving a quantity of hyperpolarized gas. The container includes at least one wall comprising inner and outer layers configured to define an enclosed chamber for holding a quantity of hyperpolarized gas. The inner layer has a predetermined thickness and an associated relaxivity value which inhibits contact-induced polarization loss of the hyperpolarized gas. The outer layer defines an oxygen shield overlying the inner layer. Of course, the two layers can be integrated into one, if the material chosen acts as a polarization-friendly contact surface and is also resistant to the introduction of oxygen molecules into the chamber of the container. The container also includes a quantity of hyperpolarized noble gas and a port attached to the wall in fluid communication with the chamber for capturing and releasing the hyperpolarized gas therethrough.

Preferably, the container material(s) are selected to result in effective $T_1$'s of greater than 6 hours for $^3$He and greater than about 4 hours for $^{129}$Xe due to the material alone. It is also preferred that the oxygen shield is configured to reduce the migration of oxygen into the container to less than about $5\times10^{-6}$ amgt/min, and more preferably to less than about $1\times10^{-7}$ amgt/min. It is additionally preferred that the inner layer thickness ("$L_{th}$") is at least as thick as the polarization decay length scale ("$L_p$") which can be determined by the equation:

$$L_p = \sqrt{T_p D_p}$$

where $T_p$ is the noble gas nuclear spin relaxation time in the polymer and $D_p$ is the noble gas diffusion coefficient in the polymer.

Advantageously, using a contact surface which has a thickness which is larger than the polarization decay length scale can minimize or even prevent the hyperpolarized gas from sampling the substrate (the material underlying the first layer). Indeed, for hyperpolarized gases which can have a high diffusion constant (such as $^3$He), surfaces with polymer coatings substantially thinner than the polarization decay length scale can have a more detrimental effect on the polarization than surfaces having no such coating at all. This is because the polarized gas can be retained within the underlying material and interact with the underlying or substrate material for a longer time, potentially causing more depolarization than if the thin coating is not present.

An additional aspect of the present invention is directed to a container with a wall formed of a single or multiple layers of materials which defines an expandable chamber. The inner surface of the wall is formed of a material which has a low relaxivity value for the (non-toxic) hyperpolarized fluid (hyperpolarized gas which is at least partially dissolved or liquefied) held therein. The wall is configured to define an oxygen shield to inhibit the migration of oxygen into the chamber. The $T_1$ of the hyperpolarized fluid held in the container is greater than about 6 hours.

In a preferred embodiment, the container of the instant invention is configured to receive hyperpolarized $^3$He and the inner layer is at least 16–20 microns thick. In another preferred embodiment, the container is an expandable polymer bag. Preferably, the polymer bag includes a metallized coating positioned over the polymer which suppresses the migration of oxygen into the polymer and ultimately into the polarized gas holding chamber. In another preferred embodiment, a third layer is added onto the metallized layer (opposite the polymer chamber) for puncture resistance. Advantageously, the captured hyperpolarized gas can be delivered to the inhalation interface of a subject by exerting pressure on the bag to collapse the bag and cause the gases to exit the chamber. This, in turn, removes the requirement for a supplemental delivery mechanism. It is additionally preferred that the container use seals such as O-rings which are substantially free of paramagnetic impurities. The proximate position of the seal with the hyperpolarized gas can make this component a dominant factor in the depolarization of the gas. Accordingly, it is preferred that the seals or O-rings be formed from substantially pure polyolefins such as polyethylene, polypropylene, copolymers and blends thereof. Of course, fillers which are friendly to hyperpolarization can be used (such as substantially pure carbon black and the like). Alternatively, the O-ring or seal can be coated with a surface material such as LDPE or deuterated HDPE or other low-relaxivity and property material and/or also preferably materials which have a low permeability for the hyperpolarized gas held in the chamber. In addition, the container can be configured such that once the gas is captured in the container to isolate a major portion of the hyperpolarized gas in the container away from potentially depolarizing components (such as fittings, valves, and the like) during transport and/or storage.

Similar to the preferred embodiment discussed above, another aspect of the present invention is a multi-layer resilient container for holding hyperpolarized gas. The container comprises a first layer of a first material configured to define an expandable chamber to hold a quantity of hyperpolarized gas therein. Preferably, the first layer has a predetermined thickness sufficient to inhibit surface or contact depolarization of the hyperpolarized gas held therein wherein the first layer material has a relaxivity value "Y". It is also preferred that the relaxivity value "Y" is less than about 0.0012 cm/min for $^3$He and less than about 0.01 cm/min for $^{129}$Xe. The container also includes a second layer of a second material positioned such that the first layer is between the second layer and the chamber, wherein the first and second layers are concurrently responsive to the application of pressure and one or both of the first and second layers acts as an oxygen shield to suppress oxygen permeability into the chamber.

Additional layers of materials can be positioned intermediate the first layer and the second layer. In one preferred embodiment, hyperpolarized gas has a low relaxivity value in the first layer material and the second layer preferably comprises a material which can shield the migration of the oxygen into the first layer. In another preferred embodiment, the resilient container has a first layer formed of a metal film (which can act both as an oxygen shield and contact surface). In this embodiment, it is preferred that the relaxivity values are less than about 0.0023 cm/min and 0.0008 cm/min for $^{129}$Xe and $^3$He respectively. Stated differently, it is preferred that the hyperpolarized gas have a high mobility on the metal surface or small absorption energy relative to the metal contact surface such that the $T_1$ of the gas in the container approaches >50% of its theoretical limit.

An additional aspect of the present invention is directed to a method for storing, transporting, and delivering hyperpolarized gas to a target. The method includes introducing a quantity of hyperpolarized gas into a multi-layer resilient container. The container has a wall comprising at least one material which provides an oxygen shield (i.e., is resistant to the transport of oxygen into the container). Preferably, the container is expanded to capture the quantity of hyperpolarized gas. The container is sealed to contain the hyperpolarized gas therein. The container is transported to a site remote from the hyperpolarization site. The hyperpolarized gas is delivered to a target by compressing the chamber and thereby forcing the hyperpolarized gas to exit therefrom. Preferably, in order to maintain the hyperpolarized state, the container is substantially continuously, from the time of polarization to the delivery, shielded and/or exposed to a proximately maintained homogeneous magnetic field to protect it from undesired external magnetic fields and/or field gradients. It is further preferred that the container be configured to be re-useable (after re-sterilization) to ship additional quantities of hyperpolarized gases.

Similarly, a further aspect of the present invention is configuring single or multi-layer resilient bags as described above with a capillary stem. The capillary stem is configured to restrict the flow of the hyperpolarized gas from the container when the valve is closed. The capillary stem is preferably positioned intermediate the container port and a valve member and, as such, forms a portion of the hyperpolarized gas (or liquid) entrance and exit path. The capillary stem is preferably configured with an inner passage which is sized and configured to inhibit the flow of the hyperpolarized gas and includes a gas contact surface formed of a polarization- friendly material. The capillary stem is preferably operably associated with a valve for the resilient container to allow the gas to be releasably captured and yet protected from any potentially depolarizing affect of the gas when the valve is closed.

Similarly, a further aspect of the present invention is configuring single or multi-layer resilient bags as described above with an isolation means for directing the gas or fluid away from the bag port during transport and storage. As such the isolation means inhibits a major portion of the hyperpolarized gas or fluid from contacting selected components (fittings, valves, O-rings) operably associated with the bag. In a preferred embodiment, the isolation means is provided by a clamp positioned to compress the portion of the bag proximate to the port to inhibit the movement of gas thereabove.

An additional aspect of the present invention is a method for preparing an expandable storage container for receiving a quantity of hyperpolarized gas. The method includes providing a quantity of substantially pure purge gas such as nitrogen or helium (preferably Grade 5 or better) into the hyperpolarized gas container and expanding the hyperpolarized gas container. The container is then collapsed to remove the purge gas. The oxygen in the container walls is outgassed by decreasing the oxygen partial pressure in the container, thereby causing a substantial amount of the oxygen trapped in the walls of the container to migrate into the chamber of the container in the gas phase where it can be removed. Preferably, after the outgassing step, the container is filled with a quantity of storage gas such as nitrogen (again, preferably Grade 5 or better). The gas is introduced into the container at a pressure which reduces the pressure differential across the walls of the container to inhibit further outgassing of the container. Preferably, the container is then stored for future use (the use being spaced apart in time from the point of preconditioning). The storage nitrogen and outgassed oxygen are removed from the container before filling with a quantity of hyperpolarized gas. Preferably, after removal from storage and prior to use, the nitrogen is removed by evacuating the container before filling with a quantity of hyperpolarized gas.

Another aspect of the present invention is directed to a method for determining the hyperpolarized gas ($^{129}$Xe or $^3$He) solubility in a (unknown) polymer or a particular fluid. The method includes introducing a first quantity of hyperpolarized noble gas into a container having a known free volume and measuring a first relaxation time of the hyperpolarized gas in the container. A substantially clean sample of desired material is positioned into the container and a second quantity of hyperpolarized noble gas is introduced into the container. A second relaxation time of the second hyperpolarized gas is measured in the container with the sample material. The gas solubility of the sample is determined based on the difference between the two measured relaxation times. The material sample can be a structurally rigid sample (geometrically fixed) with a known geometric surface area/volume which is inserted into the free volume of the chamber or container. Alternatively, the material sample can be a liquid which partially fills chamber.

Advantageously, the methods and containers of the present invention can improve the relaxation time (lengthen $T_1$) of the hyperpolarized gas or liquid or combinations of same held therein. The containers are configured such that the surface contacting the hyperpolarized gas (the hyperpolarized gas contact surface) has a minimum depth or thickness of a low-relaxivity value material relative to the hyperpolarized noble gas. Further, the containers are configured to also inhibit oxygen migration into the gas chamber of the container. In addition, the container itself can define the contact surface by forming the container out of a resilient material such as a metallic or polymer bag. Preferably, the bags are configured to inhibit the hyperpolarized gas from contacting potentially depolarizing components associated with the bag during transport or storage.

The container is preferably a multi-layer container wherein each material layer provides one or more of strength, puncture resistance, and oxygen resistance to the container. Further, at least the inner surface is configured to provide a polarization friendly contact surface. This resilient configuration provides a relatively non-complex container and increased $T_1$'s and can conveniently be re-used. The gas contact surface is preferably formed of either a polymer or a high purity metal.

Additionally, the resilient or collapsible containers can be used to deliver the gas into the patient interface without the need for additional delivery vehicles/equipment. This can reduce the exposure, handling, and physical manipulation of the hyperpolarized gas which, in turn, can increase the polarization life of the hyperpolarized gas. Resilient containers with high purity contact surfaces can be extremely advantageous for both $^{129}$Xe and $^3$He as well as other hyperpolarized gases; however, the expandable (polymer) container and coatings/layers are especially suited for hyperpolarized $^3$He. Further, the instant invention preferably positions the container with the hyperpolarized gas in a homogenous magnetic field within a shipping container to shield the gas from stray magnetic fields, especially deleterious oscillating fields which can easily dominate other relaxation mechanisms.

Additionally, the present invention can be used to determine the gas solubility in polymers or fluids which in the past has proven difficult and sometimes inaccurate, especially for helium.

Advantageously, one aspect of the present invention now provides a way to model the predictive behavior of surface materials and is particularly suited to determining the relaxation properties of polymers used as contact materials in physical systems used to collect, process, or transport hyperpolarized gases. For example, the present invention successfully provides relaxation properties of various materials (measured and/or calculated). These relaxation values can be used to determine the relaxation time ($T_1$) of hyperpolarized gas in containers corresponding to the solubility of the gas, the surface area of the contact material, and the free gas volume in the container. This information can be advantageously used to extend the hyperpolarized life of the gas in containers over those which were previously achievable in high-volume production systems.

The foregoing and other objects and aspects of the present invention are explained in detail herein.

BRIEF DESCRIPTION OF THE DRAWINGS

FIG. 5 is a detailed chart of experimental material values for Xenon and Helium.

FIG. 6 is a detailed chart of predicted material values for Xenon and Helium.

FIG. 9 is a sectional view of an alternate embodiment of a container according to the present invention.

FIG. 10 is an enlarged partial cutaway section view of the container wall according to another embodiment of the present invention.

FIG. 11 is an enlarged partial cutaway section view of an additional embodiment of a container wall according to the present invention.

FIG. 12 is an enlarged partial cutaway section view of yet another embodiment of a container wall according to the present invention.

FIG. 13 is a perspective view of a preferred embodiment of a container with a seal according to the present invention.

FIG. 14 illustrates the container of FIG. 13 with an alternative external seal according to an additional embodiment of the present invention.

FIG. 15 illustrates another container with an alternative seal arrangement according to another embodiment of the present invention.

FIG. 15A is an exploded view of the container shown in FIG. 15.

DETAILED DESCRIPTION OF THE PREFERRED EMBODIMENTS

Figure 1:
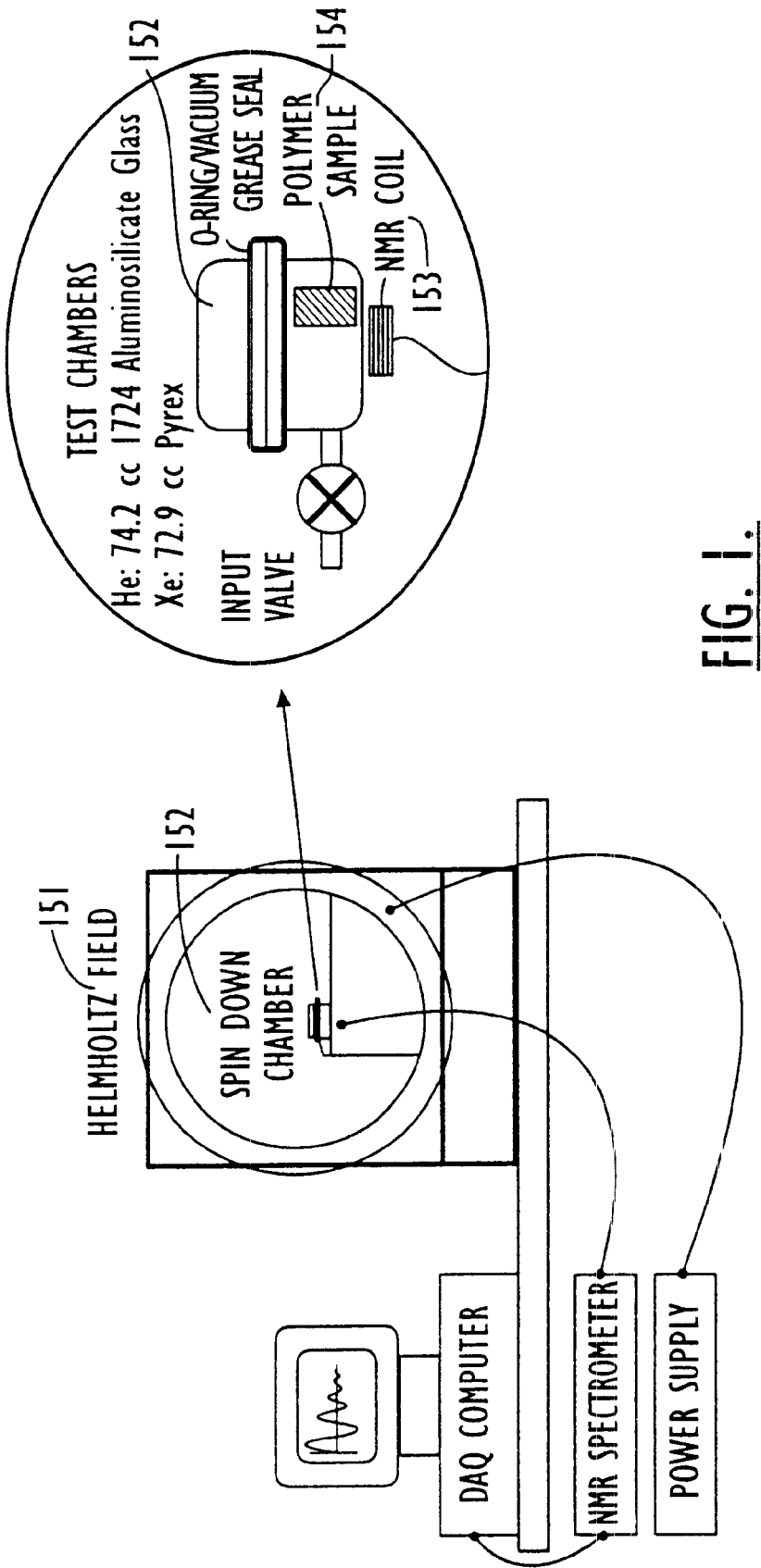
FIG. 1 is a schematic diagram of a spin-down station used to measure relaxation times according to one aspect of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers and regions may be exaggerated for clarity. For ease of discussion, the term "hyperpolarized gas" will be used to describe a hyperpolarized gas alone, or a hyperpolarized gas which contacts or combines with one or more other components whether gaseous, liquid, or solid. Thus, the hyperpolarized gas described herein can be a hyperpolarized gas composition/mixture (non-toxic such that it is suitable for in vivo introduction) such that the hyperpolarized noble gas can be combined with other noble gases and/or other inert or active components. Also, as used herein, the term "hyperpolarized gas" can include a product where the hyperpolarized gas is dissolved into another liquid (such as a carrier) or processed such that it transforms into a substantially liquid state, i.e., "a liquid polarized gas". Thus, although the term includes the word "gas", this word is used to name and descriptively track the gas produced via a hyperpolarizer to obtain a polarized "gas" product. In summary, as used herein, the term "gas" has been used in certain places to descriptively indicate a hyperpolarized noble gas which can include one or more components and which may be present in one or more physical forms.

Preferred hyperpolarized noble gases (either alone or in combination) are listed in Table I. This list is intended to be illustrative and non-limiting.

TABLE I

| Hyperpolarizable Noble Gases | | |
|---|---|---|
| Isotope | Natural Abundance (%) | Nuclear Spin |
| $^3$He | ~$10^{-6}$ | 1/2 |
| $^{21}$Ne | 0.27 | 3/2 |
| $^{83}$Kr | 11.5 | 9/2 |

TABLE I-continued

Hyperpolarizable Noble Gases

| Isotope | Natural Abundance (%) | Nuclear Spin |
|---|---|---|
| $^{129}$Xe | 26.4 | 1/2 |
| $^{131}$Xe | 21.2 | 3/2 |

Hyperpolarization

Various techniques have been employed to polarize, accumulate and capture polarized gases. For example, U.S. Pat. No. 5,642,625 to Cates et al. describes a high volume hyperpolarizer for spin polarized noble gas and U.S. Pat. No. 5,809,801 to Cates et al. describes a cryogenic accumulator for spin-polarized $^{129}$Xe. The disclosures of this patent and application are hereby incorporated herein by reference as if recited in full herein. As used herein, the terms "hyperpolarize" and "polarize" are used interchangeably and mean to artificially enhance the polarization of certain noble gas nuclei over the natural or equilibrium levels. Such an increase is desirable because it allows stronger imaging signals corresponding to better MRI images of the substance and a targeted area of the body. As is known by those of skill in the art, hyperpolarization can be induced by spin-exchange with an optically pumped alkali-metal vapor or alternatively by metastability exchange. See U.S. Pat. No. 5,545,396 to Albert et al. The alkali metals capable of acting as spin exchange partners in optically pumped systems include any of the alkali metals. Preferred alkali metals for this hyperpolarization technique include Sodium-23, Potassium-39, Rubidium-85, Rubidium-87, and Cesium-133. Alkali metal isotopes, and their relative abundance and nuclear spins are listed in Table II, below. This list is intended to be illustrative and non-limiting.

TABLE II

Alkali Metals Capable of Spin Exchange

| Isotope | Natural Abundance (%) | Nuclear Spin |
|---|---|---|
| $^{23}$Na | 100 | 3/2 |
| $^{39}$K | 93.3 | 3/2 |
| $^{85}$Rb | 72.2 | 5/2 |
| $^{87}$Rb | 27.8 | 3/2 |
| $^{133}$Cs | 100 | 7/2 |

Alternatively, the noble gas may be hyperpolarized using metastability exchange. (See e.g., Schearer, L. D., Phys. Rev., 180:83 (1969); Laloe, F. et al., AIP ConfProx #131 (Workshop on Polarized $^3$He Beams and Targets) (1984)). The technique of metastability exchange involves direct optical pumping of, for example, $^3$He without need for an alkali metal intermediary. The method of metastability exchange usually involves the excitation of ground state $^3$He atoms ($I^1S_0$) to a metastable state ($2^3S_1$) by weak radio frequency discharge. The $2^3S_1$ atoms are then optically pumped using circularly polarized light having a wavelength of 1.08 µm in the case of $^3$He. The light drives transitions up to the $2^3P$ states, producing high polarizations in the metastable state to which the $2^3S$ atoms then decay. The polarization of the $2^3S_1$ states is rapidly transferred to the ground state through metastability exchange collisions between metastable and ground state atoms. Metastability exchange optical pumping will work in the same low magnetic fields in which spin exchange pumping works. Similar polarizations are achievable, but generally at lower pressures, e.g., about 0–10 Torr.

Generally described, for spin-exchange optically pumped systems, a gas mixture is introduced into the hyperpolarizer apparatus upstream of the polarization chamber. Most xenon gas mixtures include a buffer gas as well as a lean amount of the gas targeted for hyperpolarization and is preferably produced in a continuous flow system. For example, for producing hyperpolarized $^{129}$Xe, the pre-mixed gas mixture is typically about 85–89% He, about 5% or less $^{129}$Xe, and about 10% $N_2$. In contrast, for producing hyperpolarized $^3$He, a mixture of 99.25% $^3$He and 0.75% $N_2$ is pressurized to 8 atm or more and heated and exposed to the optical laser light source in a batch mode system. In any event, once the hyperpolarized gas exits the pumping chamber it is directed to a collection or accumulation container.

A 5–20 Gauss alignment field is typically provided for the optical pumping of Rb for both $^{129}$Xe and $^3$He polarization. The hyperpolarized gas is collected (as well as stored, transported, and preferably delivered) in the presence of a magnetic field. It is preferred for solid (frozen) $^{129}$Xe that the field be on the order of at least 500 Gauss, and typically about 2 kilo Gauss, although higher fields can be used. Lower fields can potentially undesirably increase the relaxation rate or decrease the relaxation time of the polarized gas. As regards $^3$He, the magnetic field is preferably on the order of at least 5–30 gauss although, again, higher (homogeneous) fields can be used. The magnetic field can be provided by electrical or permanent magnets. In one embodiment, the magnetic field is provided by a plurality of permanent magnets positioned about a magnetic yoke which is positioned adjacent the collected hyperpolarized gas. Preferably, the magnetic field is homogeneously maintained around the hyperpolarized gas to minimize field induced degradation.

Polarized Gas Relaxation Processes

Once hyperpolarized, there is a theoretical upper limit on the relaxation time ($T_1$) of the polarized gas based on the collisional relaxation explained by fundamental physics, i.e., the time it takes for a given sample to decay or depolarize due to collisions of the hyperpolarized gas atoms with each other absent other depolarizing factors. For example, $^3$He atoms relax through a dipole-dipole interaction during $^3$He-$^3$He collisions, while $^{129}$Xe atoms relax through N-I spin rotation interaction (where N is the molecular angular momentum and I designates nuclear spin rotation) during $^{129}$Xe-$^{129}$Xe collisions. Stated differently, the angular momentum charge associated with flipping a nuclear spin over is conserved by being taken up by the rotational angular momentum of the colliding atoms. In any event, because both processes occur during noble gas-noble gas collisions, both resulting relaxation rates are directly proportional to gas pressure ($T_1$ is inversely proportional to pressure). At one atmosphere, the theoretical relaxation time ($T_1$) of $^3$He is about 744–760 hours, while for $^{129}$Xe the corresponding relaxation time is about 56 hours. See Newbury et al., "Gaseous $^3$He-$^3$He Magnetic Dipolar Spin Relaxation," 48 Phys. Rev. A., No. 6, p. 4411 (1993); Hunt et al., Nuclear Magnetic Resonance of $^{129}$Xe in Natural Xenon, 130 Phys. Rev. p. 2302 (1963). Unfortunately, other relaxation processes prevent the realization of these theoretical relaxation times. For example, the collisions of gaseous $^{129}$Xe and $^3$He with container walls ("surface relaxation") have historically dominated most relaxation processes. For $^3$He, most of the known longer relaxation times have been achieved in special glass containers having a low permeability to helium. In the past, a fundamental understanding of surface relaxation mechanisms has been elusive which has made the predictability of the associated $T_1$ difficult.

U.S. Pat. No. 5,612,103 to Driehuys et al. describes using coatings to inhibit the surface-induced nuclear spin relaxation of hyperpolarized noble gases, especially $^{129}$Xe. The contents of this patent are hereby incorporated by reference as if recited in full herein. Driehuys et al. recognized that nuclear spin relaxation of $^{129}$Xe on a polydimethoylsiloxane ("PDMS") surface coating can be dominated by dipolar coupling of the $^{129}$Xe nuclear spin to the protons in the polymer matrix. Thus, it was demonstrated that paramagnetic contaminants (such as the presence of paramagnetic molecules like oxygen) were not the dominant relaxation mechanism in that system because the inter-nuclear dipole-dipole relaxation was found to dominate the system under investigation. This was because $^{129}$Xe substantially dissolved into the particular polymer matrix (PDMS) under investigation. See Bastiaan Driehuys et al., "Surface Relaxation Mechanisms of Laser-Polarized $^{129}$Xe," 74 Phys. Rev. Lett., No. 24, pp. 4943–4946 (1995).

One aspect of the instant invention now provides a more detailed understanding of noble gas depolarization on polymer surfaces. Indeed, as will be explained further below, noble gas solubility in large numbers of polymer systems (not just PDMS) can cause inter-nuclear dipole-dipole relaxation to dominate the polarization decay rate. Notably, this insight now indicates that polymers can be especially effective for the suppression of $^3$He relaxation. In addition, a predictive explanation of noble gas relaxation on polymer surfaces is discussed below. Advantageously, it is now possible to calculate and measure the relaxation properties of various materials. This information can be advantageously used with other parameters such as free gas volume and surface area of containers to provide more effective and advantageous surface configurations and material characteristics which can facilitate, preserve, and further improve the polarization life of the noble gas. This is especially useful in providing containers which can yield reliable, repeatable, and predictable high-volume polarization production and maintenance which in the past has been difficult to achieve outside the pristine conditions of a small production laboratory.

Generally stated, magnetic interactions can alter the time constant of relaxation, referred to as the longitudinal relaxation time ($T_1$), and typically occur when different atoms encounter one another. In the case of hyperpolarized noble gases held in containers, the nuclear magnetic moments of the gas atoms interact with the surface materials to return the gas to the equilibrium or non-hyperpolarized state. The strength of the magnetic moment can be a determinative factor in determining the relaxation rate associated with the surface material. Since different atoms and molecules have different magnetic moments, relaxation rates are material-specific.

Relaxivity of Materials

In order to compare the characteristic information of certain materials concerning their respective relaxing effects on hyperpolarized noble gases, the term "relaxivity" is used. As used herein, the term "relaxivity" ("Y") is used to describe a material property associated with the rate of depolarization ("$1/T_1$") of the hyperpolarized gas sample. For a container having a chamber volume "$V_c$" capable of holding a quantity of hyperpolarized gas and for a material sample with a surface area "A" in the container chamber, each time a polarized gas atom contacts the container surface, it has a probability ("p") of depolarizing. The rate of depolarization ($1/T_1$) of this gas sample in the chamber can then be described by p times the rate at which gas atoms collide with the surface ("R").

$$\frac{1}{T_1} = Rp \tag{2.1}$$

The average surface collision rate (R) per gas atom is known from statistical mechanics, R. Reif, *Fundamentals of Statistical and Thermal Physics,* McGraw-Hill, Ch. 12–14, pp. 461–493 (1965):

$$R = \frac{vA}{4V} \tag{2.2}$$

In this equation, "v" is the mean thermal velocity of the gas atoms. For the case of a one cubic centimeter ("1 cc") sphere of $^{129}$Xe the area is $A=4\pi r^2$ and the volume is $V=4\pi r3/3$. Thus, for v=154 m/s, equation (2.2) yields a collision rate R=800 s$^{-1}$. In other words, each atom of Xe is contacting the surface of the sphere 800 times in 1 second. Therefore, according to equation (2.1) long $T_1$ times must have a minute probability for depolarization during each collision (p<<1). Substituting equation (2.2) back into equation (2.1) yields:

$$\frac{1}{T_1} = \frac{Avp}{4V} \tag{2.3}$$

Since measurements for this study are performed at room temperature, "v" will not vary. Therefore, the relaxivity term, ("Y") which is defined as Y=vp/4, results in:

$$\frac{1}{T_1} = \frac{A}{V}Y \tag{2.4}$$

Thus, relaxivity ("Y") is a material property that can describe the depolarizing effect that a specific material has on a hyperpolarized gas sample.

When considering hyperpolarized gas containers, it is important to notice the relationship between the $1/T_1$ and A/V terms in Equation 2.4. Thus, the ratio "A/V" for a sphere with a radius "r", the ratio reduces to 3/r. Therefore, a one liter sphere (1000 cc, r=6.2 cm) has a $T_1$ that is 10 times longer than a sphere with a one cubic centimeter volume (1 cc, r=0.62 cm) made of the same material. Therefore, preferably, in order to improve the $T_1$ of hyperpolarized gas in the containers, the containers are configured and sized to decrease the value of the ratio A/V—i.e., to increase the volume relative to the area of the container, as will be discussed further below.

Determining Relaxivity

Equation 2.4 can be used to calculate relaxivity of the gas if surface relaxation is the only (dominant) depolarizing effect at work. In the case of practical material studies, this is not the case. The surfaces of the test chamber, the chamber seal, and other impurities also contribute to the relaxation of the gas. However, by using the relaxation time differences between hyperpolarized gas in an empty test chamber and the hyperpolarized gas in the chamber containing a material sample positioned to contact the hyperpolarized gas, the characteristic relaxivity of the material can be determined.

Note that the relaxation rates are additive in the following form:

$$\frac{1}{T_1} = \frac{1}{T_1^a} + \frac{1}{T_1^b} + \frac{1}{T_1^c} \ldots \quad (2.5)$$

In general form, $T_1^a$ can represent the relaxation effect of the test chamber surface, $T_1^b$ can represent the effect of the hyperpolarized gas atoms colliding with one another, and so on. Assuming that surface relaxation is the dominant relaxation effect, the relaxation rate can be described by adding the surface effects of the material sample and the test chamber.

$$\frac{1}{T_1} = \frac{A_m \Upsilon_m}{V} + \frac{A_c \Upsilon_c}{V} \quad (2.6)$$

where $A_m$ and $\Upsilon_m$ describes the area and relaxivity respectively of the material sample and $A_c$ and $\Upsilon_c$ correspond to the area and relaxivity of the container or chamber. "V" is the free gas volume in the chamber. In this case, $V=V_c-V_m$, where "$V_c$" is the volume of the chamber and "$V_m$" is the volume of the container occupied by the material sample. In relaxivity studies for new materials (where the material sample is small) the free volume "V" can be reasonably approximated as equal to $V_c$, i.e., $V=V_c$. Substituting back into (2.6):

$$\frac{1}{T_1} = \frac{A_m \Upsilon_m}{V_c} + \frac{A_c \Upsilon_c}{V_c} \quad (2.7)$$

Note that for a chamber without a material sample, this equation reduces to:

$$\frac{1}{T_{1c}} = \frac{A_c \Upsilon_c}{V_c} \quad (2.8)$$

where $T_{1c}$ is the characteristic relaxation rate of the container or empty chamber. Substituting (2.8) into (2.7) yields:

$$\frac{1}{T_1} = \frac{A_m \Upsilon_m}{V_c} + \frac{1}{T_{1c}} \quad (2.9)$$

Solving equation (2.9) gives an expression for the relaxivity $\Upsilon_m$ associated with a specific material sample with a measured $T_1$ in a chamber with known volume and observed $T_{1c}$:

$$\Upsilon_m = \frac{V_c}{A_m}\left(\frac{1}{T_1} - \frac{1}{T_{1c}}\right) \quad (2.10)$$

The relaxivity of a given material can easily be translated back into a more intuitive characteristic relaxation time. One method of comparison, in keeping with past surface relaxation rate studies, is to describe the relaxation rate as if there were a 1 cc spherical cell made of the material in question. Knowing the volume and surface area of such a cell ($A=4\pi r^2$, $V=4\pi r^3/3$, $r=0.62$ cm) and substituting back into (2.8):

$$T_1^{cc} = \frac{0.207 \text{ cm}}{\Upsilon_c} \quad (2.11)$$

Again, this container geometry is for illustration as it standardizes the relaxation term for comparison with past data. For reference, observed $T_1$ values from $^{129}$Xe studies in the past showed ultra clean Pyrex with a Rb monolayer surface to have an associated $T_1^{cc}=30$ minutes.

Experimental Determination of Relaxivity

The hyperpolarized gas samples were used in a materials testing center known as the Spin Down Station. This apparatus was constructed to test various material samples in a controlled environment. The system consists of a materials testing chamber, a Pulse-NMR Spectrometer, and a LabView user interface. The flexible system allows various chambers or bags to be cleaned and filled with polarized $^{129}$Xe or $^3$He. The Pulse-NMR system then charts the deterioration of signal from these containers over time.

Equipment Layout

FIG. 1 is a schematic diagram of the Spin Down Station. This apparatus consists of a Helmholtz pair generating a stable Helmholtz magnetic field 151 around the glass test chamber labeled the Spin Down Chamber 152. The signal response frequency (f) is proportional to the applied magnetic field ($B_0$) expressed by the equation $f=\gamma B_0/2\pi$. This proportionality constant is known as the gyromagnetic ratio ($\gamma_{He}=7400$ s$^{-1}$G$^{-1}$, $\gamma_{Xe}=26700$ s$^{-1}$G$^{-1}$). If the applied magnetic field remains constant, the coil must be tuned to switch between the two gases. As an alternative to retuning, the field strength was adjusted to result in the same frequency response for both gases. A current of 1.0 A (7 G field) for $^3$He and 2.5 A (21 G field) for $^{129}$Xe was applied to the Helmholtz pair noted by the Helmholtz field shown in FIG. 1.

In the center of Helmholtz field 151 rested one of the two spin down chambers 152 used in these tests. Both chambers were valved to evacuate (base pressure ~30 milliTorr) and fill the chamber with hyperpolarized gas. Each chamber could be opened to insert polymer samples (typically 10 mm×20 mm×1 mm). As shown, the NMR coil 153 rests beneath the chamber in the center of the Helmholtz field 151.

The first spin down chamber was made of Pyrex™ coated with dimethyl dichlorosilane (DMDCS) and used a Teflon™ coated rubber O-ring as the vacuum seal. This chamber had a 110 minute characteristic $T_{1c}$ suitable for observing the surface relaxation effects of various polymer samples 154. Notably, after numerous tests, the $T_{1c}$ would often decrease. A thorough cleaning with high-purity ethanol restored the chamber to the baseline value. Unfortunately, the $T_{1c}$ for the Pyrex™ chamber with $^3$He was not long enough to distinguish good from bad materials for $^3$He. Tests of various glasses in the Pyrex™ spin down chamber showed that a chamber made of 1724 aluminosilicate glass would have a sufficiently long $T_{1c}$ for $^3$He.

The 1724 $^3$He chamber was constructed with a ground seal requiring Apiezon™ vacuum grease. The chamber had a characteristic $T_{1c}$ of 12 hours on average. The Apiezon™ grease used to seal both the chamber and the entry valve caused the chamber $T_{1c}$ to fluctuate significantly more than the Pyrex™ chamber. To restore the chamber to baseline $T_{1c}$, the grease was removed by cleaning the chamber with high-purity Hexane.

Testing Procedure

Using the Spin Down Station, seven polymer samples were tested using hyperpolarized $^{129}$Xe or $^3$He. These polymers were purchased from Goodfellow, Inc., Berwyn, Pa.

| Material | Density | Thickness (mm) ($T_1$ study) | Thickness (mm) (Sorption study) |
|---|---|---|---|
| Polyamide (Nylon 6) | 1.13 | 1 | 0.012* |
| Silicone Elastomer | 1.1–1.3 | 1 | 1 |
| High Density Polyethylene (HDPE) | 0.95 | 1 | 0.01 |
| Low Density Polyethylene (LDPE) | 0.92 | 1 | 0.05 |
| Polyimide (Kapton) | 1.42 | 1 | 0.025 |
| Polypropylene (PP) | 0.9 | 1 | 0.01 |
| Polytetrafluoroethylene (PTFE) | 2.2 | 1 | 0.01 |

*Sample provided by DuPont.

The particular polymers were chosen to represent a wide range of solubilities to $^{129}$Xe and $^3$He gases. Each polymer sample was cleaned with ethanol and cut to a specific size and shape to provide a known volume and surface area of the polymer sample (normally V=2 cm$^3$, SA=42.6 cm$^2$) for each $T_1$ study.

The following steps were taken for each material measurement:

1. Clean the testing chamber
2. Polarize $^{129}$Xe or $^3$He
3. Perform a $T_1$ study to establish the chamber baseline ($T_{1c}$)
4. Place polymer sample in chamber
5. Polarize $^{129}$Xe or $^3$He
6. Perform a $T_1$ study of the chamber containing polymer sample ($T_{1s}$)
7. Use $T_{1c}$ and $T_{1s}$ to find relaxation rate due to specific polymer

The Polymer Sorption Model

The ability to measure and calculate relaxivity can result in an understanding of the physical characteristics that differentiate materials. An initial study of a wide range of materials confirmed conventional rigid containers of glass are much better than containers of materials containing paramagnetic or ferrous constituents such as stainless steel. Notably, this test also showed a wide range of relaxivities within different material groups. In particular, different polymer materials were observed across the relaxivity spectrum. Manufacturing concerns such as durability and reliability make polymer materials an excellent alternative to the glass storage containers that are typically used for hyperpolarized gases. Scientifically, substantially pure samples of these materials allow for relatively less complex models of surface relaxation.

For discussion purposes, assume there is a polymer container of hyperpolarized gas in a homogeneous magnetic field. Since polymers are permeable materials, some quantity of gas dissolves in the container walls. The only dominant relaxation mechanism in this system is that of the hyperpolarized gas atoms interacting with the protons or contaminants in the surface and bulk of the polymer container. Driehuys et al. demonstrated that relaxation of hyperpolarized $^{129}$Xe in a specially coated glass sphere was dominated by the dipolar coupling between the protons in the surface and the $^{129}$Xe nuclear spin. See Driehuys et al., "High-volume production of laser-polarized $^{129}$Xe," 69 App. Phys. Lett. (12), p. 1668 (1996). Since Xe—Xe collisions have a 56 hour $T_1$ and typical conventional material $T_1$ times are 2 hours or less, the relaxation rate of the free gas can be neglected. Gas dissolved in the polymer surface relaxes quickly (<1 second), so most of the hyperpolarized gas in the container is in the free gas form. Therefore, relaxation of this gas occurs through continual exchange between the free gas and the gas dissolved in the polymer. In material quantities, the rate of this gas exchange can be described by the "sorption parameters"—solubility ("S"), diffusion coefficient ("D"), and permeability ("P"). Permeability is the transmission of atoms or molecules through a polymer film. It depends on chemical and physical structure of the material as well the structure and physical characteristics of the permeant molecules. Permeability can be defined as the product of solubility and the diffusion coefficient. ("P=S× D"). Solubility ("S") is a measure of how much permeant can be dissolved in a given material. Diffusion coefficient ("D") is a measure of the random mobility of the atoms in the polymer. The polymer sorption parameters can be used to characterize the relaxation of hyperpolarized gases in the presence of permeable surfaces.

Relaxation in the Presence of Polymer Surfaces

Magnetization ("M") is defined as the product of the gas polarization "P" and the gas number density "[G]", M=[G]P. The equation governing relaxation of magnetization in the presence of a surface diffusion $$\frac{\partial}{\partial t}M(x,t) = D\frac{\partial^2}{\partial x^2}M(x,t) - \Gamma M(x,t) \qquad (2.12)$$

where ("M(x,t)") is magnetization, ("D") is the diffusion coefficient of the gas in the surface material, and ("Γ") is the relaxation rate of the gas. See W. Happer et al., Hyp. Int. 38, pp. 435–470 (1987). As is customary, the solution is written as a product of spatial and time dependent components:

$$M(x,t)=m(x)e^{1/T_1} \qquad (2.13)$$

where ("m(x)") is the spatial distribution of magnetization on the surface. Substituting (2.15) into (2.13) yields the spatial equation:

$$\frac{\partial^2}{\partial x^2}m(x) = \frac{1}{D}\left(\Gamma - \frac{1}{T_1}\right)m(x) \qquad (2.14)$$

Figure 2:
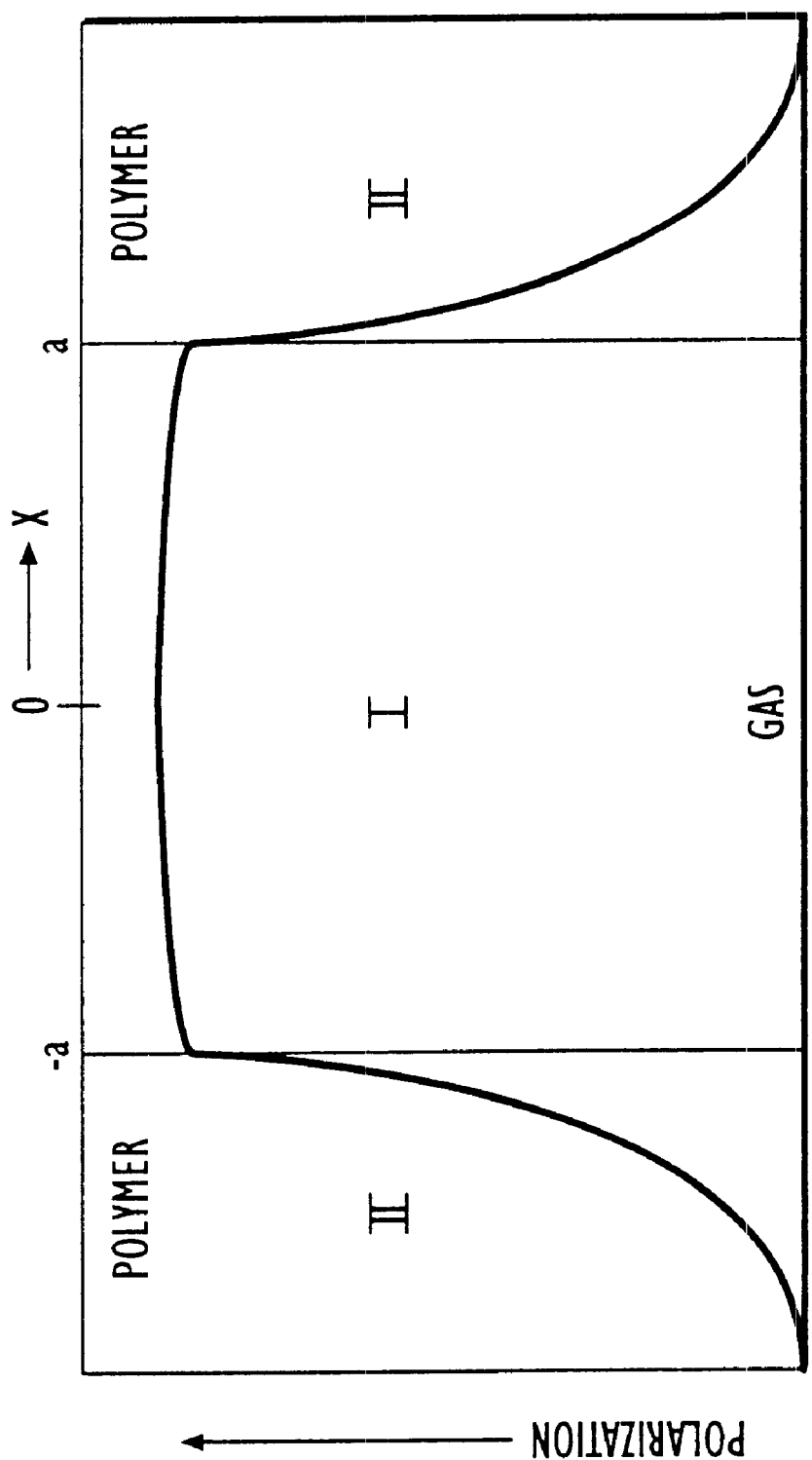
FIG. 2 is a graph showing the polarization level of a gas associated with the distance×the gas moves into a polymer.

This differential equation describes the spatial distribution of magnetization in the presence of diffusion and relaxation. The distribution of magnetization in a one-dimensional chamber is shown in FIG. 2.

The chamber is a gas volume of width "2a" bounded on each side by infinite polymer walls. The polarization of gas in this chamber has two specific regions of interest. In the free gas portion of the container, the polarization is relatively homogenous with respect to spatial variable x. In contrast, polarization drops exponentially with distance x into the polymer surface. This profile reflects a much faster relaxation rate inside the polymer as opposed to in free space.

Equation (2.14) can be used to solve for the spatial magnetization of the gas and polymer regions independently. For a gas phase with diffusion coefficient $D_g$ and intrinsic relaxation rate $\Sigma_g=0$, equation (2.14) becomes:

$$\frac{\partial^2}{\partial x^2}m_g(x) = -\frac{1}{D_g T_1}m_g(x) \quad \text{(Region I)} \tag{2.15}$$

The first order symmetric solution to this equation is:

$$m_g(x) = A\cos(k_g x) \quad k_g^2 = \frac{1}{T_1 D_g} \quad \text{(Region I)}$$

Similarly, the polymer region has diffusion coefficient "$D_p$" and relaxation rate $\Sigma_p$:

$$\frac{\partial^2}{\partial x^2}m_g(x) = -\frac{1}{D_p}\left(\Gamma_p - \frac{1}{T_1}\right)m_p(x) \quad \text{(Region II)} \tag{2.16}$$

One simplifying assumption is that the relaxation rate in the polymer is much faster than the observed relaxation rate ($\Sigma_p >> 1/T$). Thus neglecting $1/T_1$ term in (2.16) yields a solution of the form:

$$m_p(x) = Be^{-k_p(x-a)} \quad k_p^2 = \frac{\Gamma_p}{D_p} \quad \text{(Region II)}$$

These two solutions in conjunction with the appropriate boundary conditions can be used to solve for the observed $T_1$ of the gas in the polymer chamber. The first boundary condition ("BC") maintains continuity of polarization across the polymer gas boundary. Recalling that magnetization is the product of polarization and gas number density yields:

$$BC_1: Sm_g(a) = m_p(a)$$

where ("S") is defined as the ratio of gas number densities, or the Ostwald Solubility "$S=N_p/N_g$". The secondary boundary condition ("BC2") arises because the exchange of magnetization across the gas-polymer boundary is equal on both sides. This exchange, known as the magnetization current, is defined as $J_m = -D\nabla m(x)$, yielding the boundary condition:

$$BC2: D_g \frac{d}{dx}m_g(a) = D_p \frac{d}{dx}m_p(a)$$

Applying the boundary conditions to the solutions for magnetization in each of the two regions yields the following transcendental equation:

$$\tan k_g a = \frac{D_p k_p}{D_g k_g}S \tag{2.17}$$

This equation can be solved numerically, although a reasonable approximation is that $k_g a << 1$, so that $\tan k_g a \approx k_g a$. In physical terms, this implies that the magnetization is spatially uniform across the gas phase. It also considers only the slowest of multiple diffusion modes. In order for this assumption to be false, the relaxation rate at the walls would have to be fast compared to the time it takes for the gas to diffuse across the chamber. Diffusion times are typically a few seconds, while common $T_1$ values are several minutes. Applying this assumption yields:

$$k_g^2 = S\frac{D_p k_p}{D_g a} \tag{2.18}$$

Substituting in $k_g$ and $k_p$ from the solutions to (2.15) and (2.16) gives:

$$\frac{1}{T_1} = \frac{S}{a}\sqrt{\Gamma_p D_p} \tag{2.19}$$

The relaxation rate in the polymer terms can be rewritten in terms of $\Sigma_p = 1/T_{1p}$. Solving for the relaxation time $T_1$:

$$T_1 = \frac{a}{S}\sqrt{\frac{T_1^p}{D_p}} \tag{2.20}$$

This analysis can be extended into three dimensions, yielding:

$$T_1 = \frac{V_c}{A_p S}\sqrt{\frac{T_1^p}{D_p}} \tag{2.21}$$

where $V_c$ is the internal volume of the chamber, A is the exposed surface area of the polymer and S is the solubility of the gas in the polymer.

The inverse relationship between $T_1$ and S is a key observation from this development. Because He solubilities are typically many orders of magnitude lower than corresponding Xe solubilities, $T_1$ times for $^3$He should be significantly longer than for $^{129}$Xe. There is also an apparent inverse square root dependence on the diffusion coefficient $D_p$. However, the relaxation time in the polymer $1/T_p$ also depends on $D_p$, canceling the overall effect on $T_1$. This leaves solubility as the dominant sorption characteristic in determining $T_1$.

Despite canceling out of (2.21) the diffusion coefficient plays a significant role in another quantity of interest, the length scale of the gas and polymer interaction. The exponential decay length scale of the polarization $L_p = 1/k_p$ is given by the solution to (2.16):

$$L_p = \sqrt{D_p T_1^p} \tag{2.22}$$

Importantly, this scale describes the depth into the polymer that the gas travels in the relaxation time period. In order to compare theoretical predictions to experimental data, it is preferred that material samples be at least several length scales thick. This ensures that the surface model developed here which assumes infinite polymer thickness is an accurate approximation of the diffusion process. For reference, LDPE has a diffusion constant of 6.90e-6 cm$^2$/s for helium gas and hyperpolarized $^3$He has a relaxation time in the polymer of about 0.601s ($T_1^P$=0.601 seconds). The resulting length scale is about 20 $\mu$m, many times smaller than the 1 mm polymer samples used in the study described herein.

Predicting $T_1$ Values Using Sorption Model

Using equation (2.21) to predict $T_1$ values for hyperpolarized gases in the presence of various polymer surfaces requires knowledge of the test environment ($V_c$, $A_p$), as well as parameters linking the specific gas and polymer ($T_1^P$, S and D). Unfortunately, the solubility and diffusion data linking gas and polymers is scattered and sometimes nonexistent. On the other hand, the test environment is typically known. Advantageously, this data can be used to calculate the $T_1^P$.

As discussed earlier, the relaxation mechanism that dominates hyperpolarized gas relaxation in polymers is the interaction with the nuclear magnetic moments of the hydrogen nuclei (in hydrogen based polymers). Generally stated, in the absence of paramagnetic contaminants, the $^1H$ nuclei are the only source of magnetic dipoles to cause relaxation. Based on this interaction, Huang and Freed developed an expression for the relaxation rate of spin ½ gas diffusing through a polymer matrix. See L. P. Hwang et al., "Dynamic effects of pair correlation functions on spin relaxation by translational diffusion in liquids," 63 J. Chem. Phys. No. 9, pp. 4017–4025 (1975); J. H. Freed, "Dynamic effects of pair correlation functions on spin relaxation by translational diffusion in liquids. II. Finite jumps and independent $T_1$ processes," 68 J. Chem. Phys. Vol. 9, pp. 4034–4037 (1978); and E. J. Cain et al., "Nuclear Spin Relation Mechanisms and Mobility of Gases in Polymers," 94 J. Phys. Chem. No. 5, pp. 2128–2135 (1990). This results in the following expression in a low magnetic. field B regime (B<1000 Gauss).

$$T_1^p = \frac{405}{32\pi} \frac{D_p^b}{s(s+1)\gamma_G^2\gamma_H^2 h^2 N_a[^1H]} \quad (2.23)$$

In this formula, $\gamma_g$ is the gyromagnetic ratio of the noble gas, $\gamma_H$ is the gyromagnetic ratio of the protons, s is the proton spin number (½), $N_a$ is Avogadro's number, [$^1H$] is the molar density of protons in the matrix, and b is the distance of closest approach of the noble gas to a proton. The dipole interaction equations have an inverse square dependence on the gyromagnetic ratios $\gamma_g$ and $\gamma_h$. As noted before, substituting this form into Equation (2.21) cancels $D_p$ from the relaxation expression. This leaves only solubility (S) to effect the $T_1$ in various polymers. The other significant factor in (2.23) is the $[^1H]^{-1}$ dependence. As such, since protons in the polymer are the dominant relaxation mechanism, high concentrations will adversely affect $T_1$.

Implementing this expression for $T_1^P$ requires the appropriate physical parameters in CGS units. Table 2.1 shows an example of the approximate values used for this calculation performed for relaxation of $^{129}Xe$ in low-density polyethylene (LDPE):

TABLE 2.1

Sample Data for $T_1^P$ of $^{129}Xe$ in LDPE $\gamma_g$ (G$^{-1}$s$^{-1}$) = 7.40e03
$\gamma_h$ (G$^{-1}$s$^{-1}$) = 2.68e04
h (erg s) = 6.63e-27
[$^1H$] (mol/L) = 131.43
b (cm) = 2.40e-08
$D_g$ (cm$^2$s$^{-1}$) = 6.90e-08
$T_1^P$ (s) = 0.0653

*One of few available literature values (Polymer Handbook)

Confirmation of Predictive Model

The development of the sorption based relaxation model along with the experimental apparatus to test relaxivity allows the comparison of a theoretical model of surface relaxation with experimental results. Confirmation of this model enables quantitative predictions of surface relaxation for selecting appropriate and preferred materials to contact hyperpolarized gases. The spin down station was used to measure the relaxation effects of 7 different polymers on hyperpolarized $^{129}Xe$ and $^3He$. In order to compare this experimental data with the theoretical, solubility of both gases in each polymer was measured. These sorption measurements are described below as well as a discussion of results from the $^{129}Xe$ and $^3He$ polymer studies.

Solubility Measurements

Solubility ("S") is the only remaining unknown in the formula to predict $T_1$ of hyperpolarized gases in polymers (2.21). The equation is restated here for reference:

$$T_1 = \frac{V_c}{A_p S} \sqrt{\frac{T_1^p}{D_p}}$$

Sorption data for various polymers is tabulated in sources such as the Polymer Handbook. S. Pauly, *Permeability and Diffusion Data,* The Polymer Handbook VI/435. Unfortunately, while data for helium is widely available (although prone to error), there has not been a need to measure sorption characteristics of Xe in different polymers. The lack of published xenon solubilities resulted in a search for equipment to measure these quantities. The polymer group at the Chemical Engineering Department at North Carolina State University measured the solubility of both xenon and helium gases in the 7 polymers that were to be used to verify the polymer relaxation theory. The results of helium and xenon solubility measurements are compared to the available literature values in Table 4.1 below (note that some data was not available).

|  | S(Xe) (lit.) | S(Xe) (meas.) | S(He) (lit.) | S(He) (meas.) |
| --- | --- | --- | --- | --- |
| LDPE | 0.59 | 0.68± | 0.0055 | 0.006± |
| HDPE | — | 0.42± | 0.0028 | 0.004± |
| PP | — | 0.70± | 0.0002 | 0.020± |
| PTFE | 0.75 | 0.70± | 0.1104 | 0.003± |
| Nylon 6 | — | .31 | 0.0043* | 0.003 |
| Silicone | 3.99 | 1.93± | 0.0430 | 0.034± |
| PI | — | 4.00 ± 0.1 | 0.0056 | 0.030± |

*Literature value for Nylon 11.

Table 4.1: Results of Solubility Measurements

The measurements were obtained by placing polymer samples in an evacuated chamber. A known pressure of gas was then introduced into the chamber. As the gas dissolved into the polymer, the decrease in chamber pressure was recorded. By knowing the volume of the test chamber and carefully maintaining the temperature of the apparatus, the solubility of the gas in the polymer can be calculated from the pressure vs. time data. However, there are many intrinsic difficulties in polymer sorption measurements. Because of the low diffusion coefficients in some polymers such as polyimide, it can take a long time for gas to permeate the entire sample and establish equilibrium. Even the thinnest samples available must be allowed to remain in the chamber for many days. Another problem, evident in He measurements, is that pressure differences observed for materials with low solubilities are extremely small, resulting in significant measurement uncertainty. In addition these to problems, density values play an important role in the solubility calculation. While the manufacturer provides density estimates for the material samples, laboratory measurements confirmed that these values were often inaccurate.

This discrepancy can be responsible for dramatic changes in the final solubility value. It should therefore be noted that relative to the sorption measurements, more reliable results could be obtained. However, the values provided are sufficient to confirm the solubility based relaxation theory.

$^{129}$Xe Materials Study

The majority of this materials study was performed using hyperpolarized $^{129}$Xe. A much greater sensitivity of $^{129}$Xe to surface effects resulted in shorter $T_1$ times and allowed for more rapid testing of materials. More dramatic relaxation effects eliminate the need for an extremely long chamber $T_1$ as is the case for $^3$He studies. This fact alone resulted in more reliable results for $^{129}$Xe materials testing.

Figure 3:
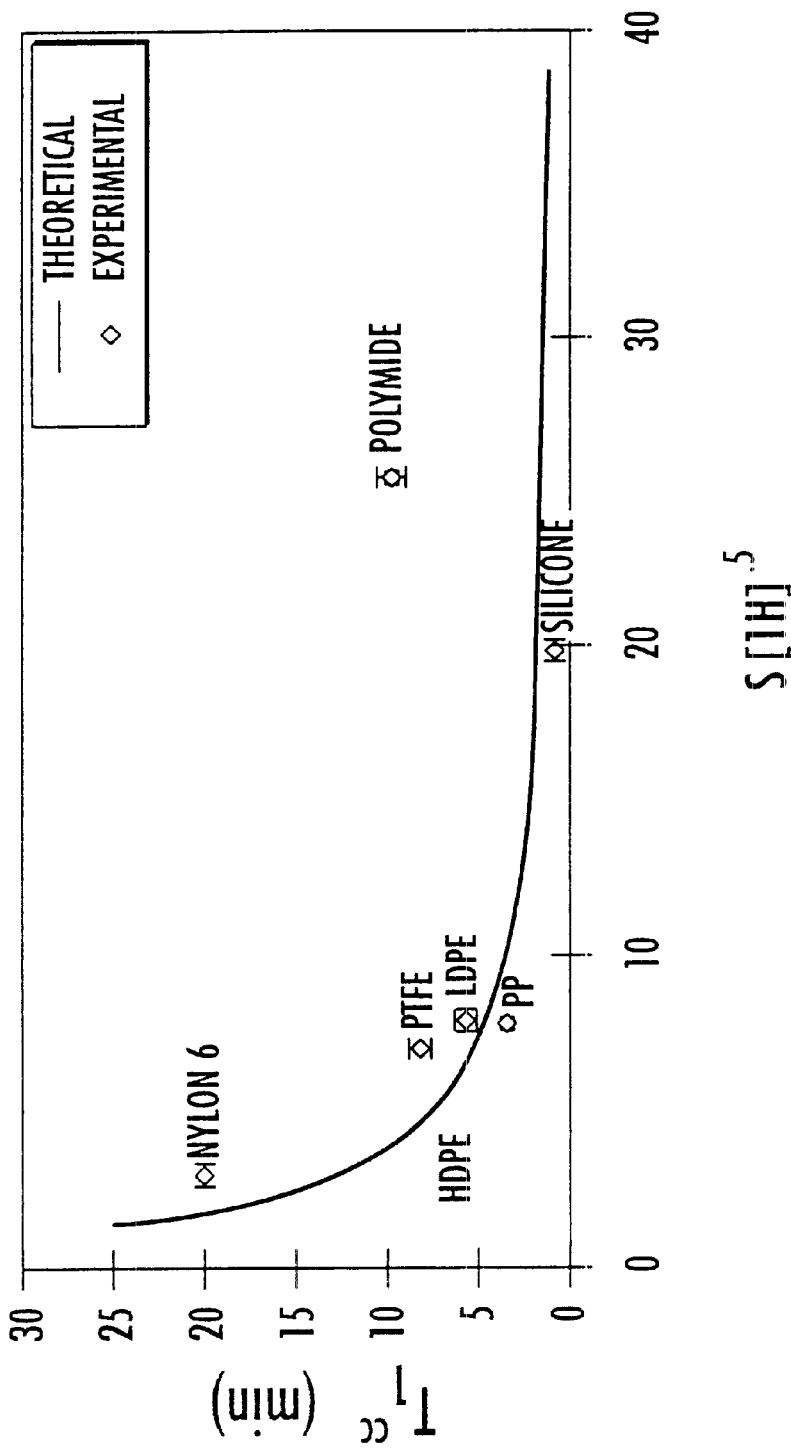
FIG. 3 is a graph showing the results of the standardized relaxation times plotted against solubility (measured and theoretical) for various materials ($T_1^{cc}$ representing the relaxation time for $^{129}$Xe hyperpolarized gas in a one cubic centimeter sphere).

FIG. 3 is a plot of $T_1^{cc}$ vs. the product $S[1H]^{0.5}$, representing the two significant terms in the expression for $T_1$ (2.21) developed in the polymer sorption relaxation model. For the experimental data points, the y error bars on the graph represent the cumulative error in the relaxation measurement. The x error bars are associated with the solubility measurements described above. The data confirms that solubility can be used to predict $T_1$ for hyperpolarized $^{129}$Xe on polymer surfaces. While the experimental data points follow the trend predicted by the theoretical model remarkably well, certain discrepancies merit further discussion.

Lower than predicted $T_1$ measurements as in the case of silicone can be explained in several ways. Paramagnetic impurities in the material sample or test chamber are the primary suspect. Recall that only protons were assumed to have a depolarizing effect on the hyperpolarized gas. In order for this assumption to hold true, the composition of the material sample would have to be extremely pure. For example, given that the gyromagnetic ratios of Fe and protons are related $Y_{Fe}\sim 1000Y_{1H}$, a one part per thousand presence of Fe in the material sample can double the relaxation rate. Although the sample surfaces were cleaned with high-purity ethanol prior to testing in the Spin Down Station, paramagnetic impurities can be trapped in the polymer matrix during the curing process. One possible contaminant is Pt metal (which is paramagnetic) that can be used in the mold forming silicone polymers.

When considering factors that cause the measured $T_1$ results to be higher than predicted as in the case of polyimide (PI) and PTFE, the diffusion coefficient becomes an important parameter. For polyimide, the diffusion of Xe into the polymer is so slow that it takes weeks for the Xe to equilibrate completely. This time scale is much longer than the 1–2 hour time scale of the relaxation measurements. Since the $T_1^p$ of $^{129}$Xe in PI is on the order of 100 ms (based on LDPE), the $^{129}$Xe atoms only sample a tiny layer (~5 µm, based on a diffusion coefficient $D\sim 10^{-8}$ cm$^2$/s), of the surface of the polymer sample. This surface layer may have different sorption characteristics than the bulk polymer that was used in the solubility measurements. While solubility can typically only be measured for the bulk sample, the region of interest is only 0.5 µm out of 1 mm, or $0.5\times 10^{-6}/1.0\times 10^{-3}$ (about 1/2000) of the actual sample.

A summary comparison of the predicted and measured results for $^{129}$Xe is presented in Table 4.2. More detailed results from the theoretical and experimental calculations are tabulated in FIGS. 5 and 6.

TABLE 4.2

Results of Polymer Relaxation Study for $^{129}$Xe

| | S | Pred. Y (cm/min) | Pred. $T_1^{cc}$ (min) | Measured Y (cm/min) | Measured $T_1^{cc}$ (min) |
|---|---|---|---|---|---|
| LDPE | 0.68 | 0.0419 | 4.94 | 0.0370 ± 0.0039 | 5.59 ± 0.59 |
| HDPE | 0.42 | 0.0263 | 7.87 | 0.0362 ± 0.0025 | 5.71 ± 0.39 |
| PP | 0.70 | 0.0427 | 4.85 | 0.0540 ± 0.0035 | 3.83 ± 0.25 |
| PTFE | 0.75 | 0.0356 | 5.82 | 0.0249 ± 0.0016 | 8.30 ± 0.54 |
| Nylon 6 | .31 | .0166 | 12.5 | 0.0104 ± 0.0016 | 19.91 ± 2.99 |
| Silicone | 1.93 | 0.1066 | 1.94 | 0.3112 ± 0.0072 | 0.67 ± 0.02 |
| PI | 4.10 | 0.1345 | 1.54 | 0.0212 ± 0.0017 | 9.78 ± 0.78 |

$^3$He Material Studies

Figure 4:
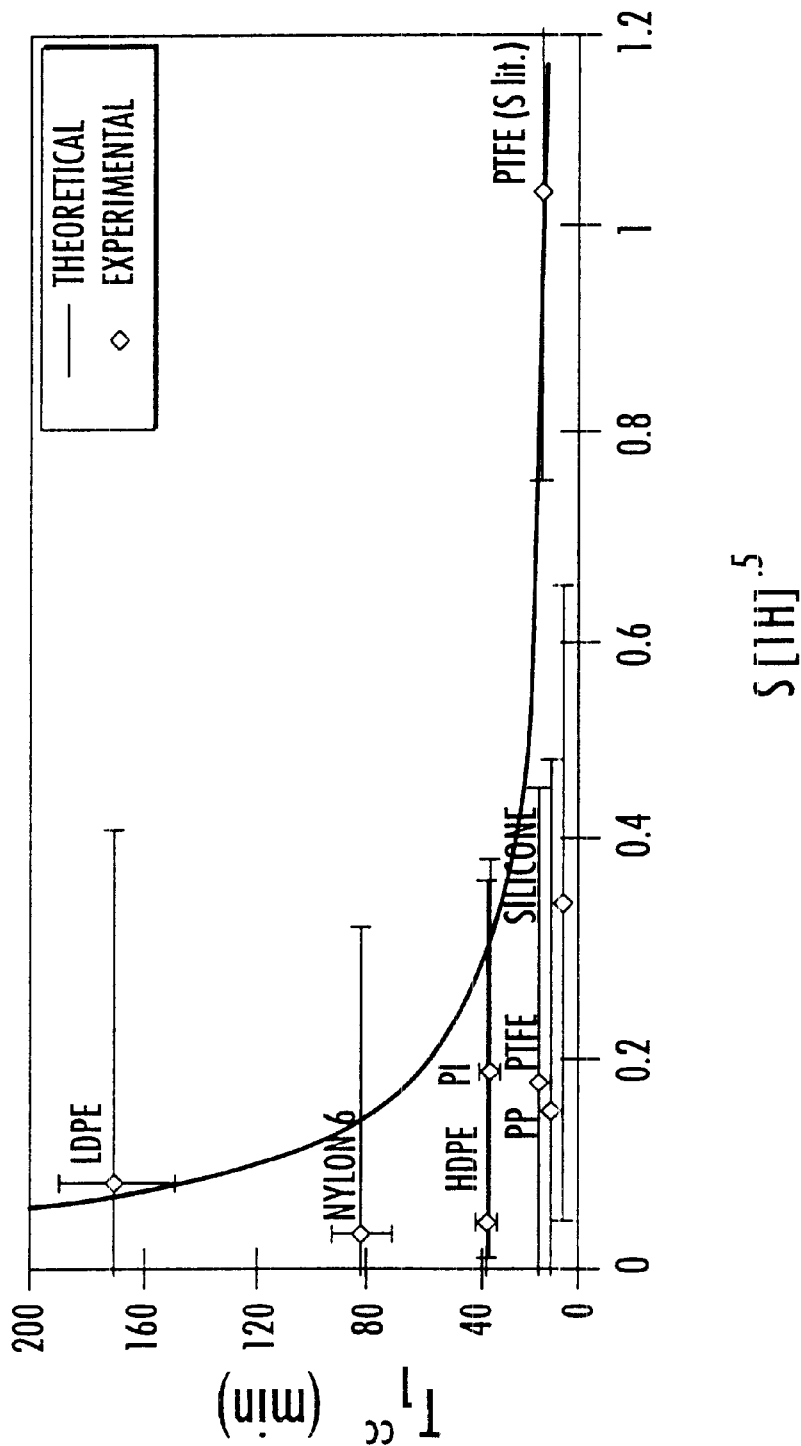
FIG. 4 is a graph similar to FIG. 3 showing the results of standardized relaxation times for $^3$He.

The study of $^3$He surface relaxation on polymers is much more challenging than the study of $^{129}$Xe. FIG. 4 shows the results of this study in the $T_1^p$ vs. $S[1H]^{0.5}$ form as discussed for the $^{129}$Xe presented in FIG. 3. The various errors associated with the $^3$He study make direct comparison with the $^{129}$Xe difficult. However, there are trends linking the two studies worth noting.

The results for LDPE and PTFE agree extremely well with theory. However, the other materials in the $^3$He study fall short of predicted $T_1$ relaxation times. Of these materials, silicone, PP and HDPE are consistent with short results observed in the $^{129}$Xe study.

This trend points to paramagnetic impurities in the material samples. These contaminants can include dust, fingerprints, Apiezon grease, and ferrous impurities that may be trapped in the polymer material. Unfortunately, higher diffusion coefficients for He result in much longer length scales (~20 µm $^3$He vs.~1 µm $^{129}$Xe, Equation 2.23) for polymer gas interaction. The greater mobility of gas atoms in the polymer results in much deeper sampling of the polymer. This sampling could significantly increase the probability of interaction with paramagnetic impurities if their distribution in the polymer is non-uniform. For example, gas in silicone has a large diffusion coefficient (DHe~4e-5, DXe~5e-6) relative to other polymers in the study. While the measured $T_1$ for silicone, PP, and HDPE was lower than predicted in both $^{129}$Xe and $^3$He studies, the $^3$He has a length scale roughly 3 times that of $^{129}$Xe. This contaminant concern magnifies the importance of sample preparation in the study of surface effects as well as the preparation of containers used for hyperpolarized gases. As discussed with the $^{129}$Xe study, sample preparation included only a surface cleaning, leaving any contaminants contained within the polymer matrix. One alternative can be to use acid baths to clean containers or container materials to remove or minimize at least surface and proximate sub-surface impurities potentially embedded in the polymer matrix.

Of the remaining polymers in the $^3$He study, only polyimide (PI) and nylon 6 show markedly different results between the two studies. One distinction that might explain this result is the difference between amorphous and semicrystalline polymers. LDPE, HDPE, and PP are amorphous polymers that should exhibit uniform solubility. Alternatively, semicrystalline polymers such as PTFE, nylon 6, and PI might exhibit spatial diffusion and thus exhibit regional solubilities that differ from the bulk solubility measured in the polymer lab.

A summary comparison of the predicted and measured results for $^3$He is presented in Table 4.3. (Detailed results in FIGS. 5 and 6).

TABLE 4.3

Results of Polymer Relaxation Study for ³He

| | S | Pred. Y (cm/min) | Pred. $T_1^{cc}$ (min) | Measured Y (cm/min) | Measured $T_1^{cc}$ (min) |
|---|---|---|---|---|---|
| LDPE | 0.0060 | 0.0012 | 170.98 | 0.0012 ± 0.00015 | 170.80 ± 21.22 |
| HDPE | 0.0040 | 0.0008 | 252.40 | 0.0056 ± 0.00055 | 36.65 ± 3.66 |
| PP | 0.0067 | 0.0013 | 154.81 | 0.0211 ± 0.00156 | 9.80 ± 0.77 |
| PTFE | 0.1104 | 0.0158 | 13.09 | 0.0150 ± 0.00071 | 13.72 ± 0.65 |
| Nylon 6 | .003 | .0005 | 395 | 0.0026 ± 0.00034 | 79.98 ± 11.17 |
| Silicone | 0.0340 | 0.0061 | 33.69 | 0.0386 ± 0.00169 | 5.36 ± 0.22 |
| PI | 0.0300 | 0.0032 | 64.30 | 0.0055 ± 0.00054 | 37.58 ± 3.78 |

$O_2$ Contamination

Impurities introduced into the test environment could also account for measurement errors. Dust, fingerprints, and other contaminants may be introduced into the test chamber when the chamber is opened to insert the sample. All of these contaminants have a depolarizing effect that is not included in the sorption model. The most significant confirmed contaminant in the test environment is the presence of $O_2$ in the test chamber.

Because $O_2$ has a magnetic moment, it can relax hyperpolarized gases in the same manner as protons. While $O_2$ affects $^{129}Xe$ and $^3He$ similarly, the longer $T_1$ times associated with the $^3He$ study magnify any $O_2$ contamination. For example, 1 Torr of $O_2$ in the chamber would generally not be noticed on the time scale of the $^{129}Xe$ study but would have a radical impact on $^3He$ studies. The effect of $O_2$ in the test chamber was observed on several occasions. It resulted in a nonexponential decay rate many times faster than the predicted $T_1$ of the sample.

While in storage, oxygen from the atmosphere diffuses and sorbs into the polymer sample. In order to remove this $O_2$ from the polymer, the sample is preferably left under vacuum for a period of time before testing. The time period necessary for this degassing to take place can be calculated if diffusion coefficients are available. Table 4.5 shows the degassing calculations for 1 mm thick polymer samples with available $O_2$ diffusion coefficients, assuming $t \sim (Z)^2/D$ (Z=sample thickness).

TABLE 4.5

$O_2$ Degassing Time for ³He Relaxation Studies

| Material | $D(O_2)$ cm²/s | Volume $O_2$ in Polymer cc (STP) | Vacuum Time Hr |
|---|---|---|---|
| LDPE | 6.80e-06 | 0.0201 | 0.41 |
| HDPE | 3.07e-06 | 0.0077 | 0.90 |
| PP | 1.95e-05 | * | 0.14 |
| PTFE | 8.11e-07 | 0.0893 | 3.43 |
| Silicone | 4.10e-05 | 0.1302 | 0.07 |

*no $S(O_2)$ available for PP

In determining the relaxation time ($T_1$) of a hyperpolarized noble gas in a polymer container, equation 2.21 can be restated as:

$$T_1 = \frac{V}{AS}\sqrt{\frac{T_1^p}{D_p}} \quad (2.21)$$

where "V" is the container volume, "A" is the container surface area, "S" is the Ostwald solubility of the noble gas in the polymer, "$T_1^p$" is the relaxation time of the noble gas dissolved in the polymer matrix, and "$D_p$" is the diffusion coefficient of the noble gas in the polymer. This quantitative analysis reveals that the relaxation time of the noble gas is inversely proportional to noble gas solubility in the polymer. Indeed, and surprisingly, as noted above, the surface induced relaxation time is believed to be proportional to the square root of the noble gas relaxation time in the polymer matrix.

Restating the multiple constants of equation 2.23 into a factor "C" results in:

$$C = \frac{32\pi\hbar^2 Na}{4.05 \times 10^5} \quad (2.23a)$$

Thus, the relaxation rate of a noble gas in the polymer can be expressed as stated in $$\frac{1}{T_1^p} = \frac{C\gamma_G^2\gamma_H^2 I(I+1)}{bD_p}[^1H] \quad (2.23b)$$

equation (2.23b (I=proton spin)).

Inserting this relaxation rate expression into equation (2.21') shows that the dependence on diffusion coefficient disappears and results in a surface relaxation time "$T_1$" which can be expressed by equation (2.23c).

$$T_1 = \frac{V}{AS\gamma_G\gamma_H}\sqrt{\frac{b}{CI(I+1)}}[^1H] \quad (2.23c)$$

This expression can be used to predict the relaxation time of hyperpolarized noble gases such as either $^3He$ or $^{129}Xe$ on any polymer surface. As was pointed out in U.S. Pat. No. 5,612,103, perdeuteration of the polymer should lead to improvement in the noble gas relation time. However, this improvement appears to be less than what was previously predicted. The gyromagnetic ratio $\gamma_D$ of deuterium is 6.5 times smaller than for hydrogen, and the spin "I" is 1. A comparison of the relaxation time of the noble gas in the perdeuterated polymer matrix versus its normal counterpart shows the following:

$$\frac{T_p(D)}{T_p(H)} = \frac{(1/2)(1/2+1)(26750)^2}{(1)(1+1)(4106)^2} = 15.9 \quad (2.30)$$

However, this improvement in $T_p$ translates into an overall improvement in relaxation time of about 4 (the square root of 15.9). Thus, deuteration is still desired but perhaps is not as impressive as was previously expected.

A comparison of $^3He$ relaxation with $^{129}Xe$ relaxation on a given polymer surface can now be made using equation (2.23c) assuming that "b" does not vary substantially for the two gases as expressed in equation (2.31).

$$\frac{T_1(^3He)}{T_1(^{129}Xe)} = \frac{S_{Xe}\gamma_{Xe}}{S_{He}\gamma_{He}} \quad (2.31)$$

For example, in low-density polyethylene ("LDPE"), the ratio of xenon solubility to helium solubility is 107 and the ratio of $\gamma_{Xe}/\gamma_{He}=0.37$. Thus, the relaxation time of $^3He$ on a LDPE surface will be nearly 40 times longer than for $^{129}Xe$.

Further, as noted above, the noble gas polarization level is not spatially uniform in the polymer. The polarization is constant for the gaseous phase but falls off exponentially with distance into the polymer.

Therefore, it is important to note that especially in the case of polymer coatings, the thickness of the coating preferably exceeds the polarization decay length scale "$L_p$" (equation 2.22) in order for the gas depolarization time to depend on the polymer properties in a predictable way. For a coating thickness less than "$L_p$", polarized gas can sample the substrate underneath the polymer, and potentially undergo undesirably fast relaxation. Because "$T_p$" also depends linearly on "$D_p$," the depolarization length scale is proportional to the gas diffusion coefficient. Thus, especially for $^3$He, which tends to have a high diffusion constant, the polymer contact layer, or the thickness of the coating or film is preferably several times the critical length scale. Preferably, the thickness is above about 16 micrometers and more preferably at least 100–200 micrometers thick in order to be effective. In fact, coatings that are substantially thinner than "$L_p$" can be more deleterious than having no coating at all, because the mobility of the noble gas once into the coating is reduced. As such, a noble gas dissolved in a thin coating can interact with the surface underneath for a much longer period of time than if the coating were not present. Indeed, the probability of depolarization appears to increase as the square of the interaction time.

The relatively long relaxation times achievable with polymers (coatings or container materials) make the development of polymer bags for hyperpolarized gas storage appealing. Further, bags are a desirable storage and delivery device for magnetic resonance imaging using inhaled hyperpolarized $^3$He because the gas can be completely extracted by collapsing the bag. In contrast, a rigid container typically requires a more sophisticated gas extraction mechanism.

$O_2$ Induced Relaxation

When bags with long surface relaxation times are used, other relaxation mechanisms can become important. One of the most important additional relaxation mechanisms is due to collisions of the noble gas with paramagnetic oxygen as noted above. Saam et al. have shown that the relaxation time of $^3$He due to collisions with paramagnetic oxygen can be expressed as stated in equation (2.32).

$$T_1[O_2]=2.27 \text{s amgt} \quad (232)$$

(Note amagat is abbreviated as "amgt")(1 amagat=2.689× $10^{19}$ atoms/cm$^3$, the density of an ideal gas at 273K and 1 atm.). See B. Saam et al., "Nuclear relaxation of $^3$He in the presence of $O_2$," Phys. Rev. A, 52, p. 862 (1995). Thus, a pressure of oxygen as small as 1/1000 of an atmosphere can result in a $^3$He relaxation time of only 38 minutes even with perfect surfaces. Given this problem, tremendous care should be taken to reduce the oxygen content in the storage container through careful preconditioning of the container, such as by pumping and pure gas purging methods. However, even with preconditioning, a bag is susceptible to permeation of oxygen through the polymer which can disadvantageously build substantial oxygen concentration over time. The volume of oxygen transmitted through the polymer material depends on several factors, including the polymer-specific oxygen permeability coefficient "$Q_{O2}$". For small quantities of oxygen transfer, the rate of oxygen concentration build-up in the bag is nearly constant, and can be expressed by equation (2.33).

$$\frac{d}{dt}[O_2] = \frac{A \Delta P_{O2}}{V_{bag} \Delta x} Q_{O2} \quad (2.33)$$

"[$O_2$]" is the oxygen concentration in the bag, "A" is the polymer surface area, "$\Delta P_{O2}$" is the oxygen pressure difference across the bag surface, "$V_{bag}$" is the volume of the bag, "$\Delta x$" is the polymer thickness, and "$Q_{O2}$" is the oxygen permeability coefficient. Using equation (2.33) and a bag having the following characteristics (area=648 cm, volume=1000 cm$^3$, $\Delta x$=0.01 cm, P=0.2×10$^5$Pa, $Q_{O2}$ (LDPE)=2.2×10$^{-13}$ cm$^2$/s Pa) gives a d/dt($O_2$) value of about 2.8×10$^{-7}$ amgt/s. Thus, a one hour duration (3600 seconds) will give 1×10$^{-3}$ amgt, which corresponds to a $T_1$ of about 38 minutes. For Tedlar™, the $O_2$ permeability is smaller (0.139×10$^{-13}$ cm$^2$/s Pa- 158 times less permeable than LDPE). Thus, in this material, one hour of permeation will give an $O_2$ induced $T_1$ of about 99 hours, but after 10 hours the $T_1$ drops to only 10 hours. Thus, as an alternative to an $O_2$ shield placed over the inner layer, the contact surface layer itself can be formed as a polymer having reduced permeability to $O_2$ and/or with increased thickness $\Delta x$.

Accordingly, oxygen-induced relaxation can quickly dominate surface relaxation even when careful gas handling techniques are employed. Therefore, in order to make polymer bags a viable storage medium, another layer of material is preferably used to suppress oxygen permeability. So long as the thickness of polymer in contact with the polarized gas is greater than $L_p$, the secondary material used for oxygen permeability suppression does not need to be non-depolarizing. A metal film such as aluminum can be very effective in such an application.

Materials

A comparison of the experimentally measured relaxation times to the theoretical values reveals remarkable agreement for the polymer systems for which $^{129}$Xe solubilities are known. Theoretical relaxation times are also calculated for $^3$He on a variety of polymer surfaces/systems. The results are summarized in FIGS. 5 and 6. The relaxation times have been scaled to a 1 cm$^3$ spherical container.

Note that the results for $^{129}$Xe in the fluoropolymer PTFE (Teflon™) are also shown in FIGS. 5 and 6. For this case, for a one cubic centimeter ("cm$^3$") spherical container, the calculated $T_1$ was 5.65 min and the observed relaxation time was 8.3 min. The calculations are identical to those discussed previously except for the substitutions in the equations and a subtle change in "b" due the larger size of the fluorine atom compared to the hydrogen atom. The composition of the atomic structure of the material is different (i.e., fluorine versus a hydrogen atom). In fact, with the possible exception of Tedlar™ (polyvinylfluoride), most fluoropolymers are not preferred for the preservation of $^3$He hyperpolarization. For example, the predicted $T_1$ for $^3$He on PTFE is only 13.1 minutes in a I cm$^3$ sphere. This is due to a relatively high solubility of helium in most fluropolymers due to that larger void space in the polymer resulting from the large fluorine atoms. Furthermore, most common gasket materials such as Viton™, Kel-F™, and Kalre™, are fluropolymers with fillers and can potentially be substantially depolarizing to $^3$He as compared to pure hydrocarbon gaskets such as those containing polyolefins. Examples of preferred seal materials include polyolefins such as polyethylene, polypropylene, and copolymers and blends thereof.

Because the shape of the container (the gas holding chamber area) can impact the rate of depolarization, it is preferred that container configurations be selected to maximize the free-gas volume of the container (V) while minimizing the surface area (A) which contacts the hyperpolarized gas (that is, to decrease the value of the ratio A/V). More preferably, the container is sized and configured to provide a A/V ratio of about less than 1.0 cm$^{-1}$, and even more preferably less than about 0.75 cm. In one embodiment, the container is substantially spherical, such as a round balloon-like container.

Preferred polymers for use in the inventions described herein include materials which have a reduced solubility for the hyperpolarized gas. For the purposes of the inventions herein, the term "polymer" is broadly construed to include homopolymers, copolymers, terpolymers and the like. Similarly, the term "blends and mixtures thereof" includes both immiscible and miscible blends and mixtures. Examples of suitable materials include, but are not limited to, polyolefins (e.g., polyethylenes, polypropylenes), polystyrenes, polymethacrylates, polyvinyls, polydienes, polyesters, polycarbonates, polyamides, polyimides, polynitriles, cellulose, and cellulose derivatives and blends and mixtures thereof. It is more preferred that the coating or surface of the container comprise one or more of a high-density polyethylene, low density polyethylene, polypropylene of about 50% crystallinity, polyvinylchloride, polyvinylflouride, polyamide, polyimide, or cellulose and blends and mixtures thereof.

Of course, the polymers can be modified. For example, using halogen as a substituent or putting the polymer in deuterated (or partially deuterated) form (replacement of hydrogen protons with deuterons) can reduce the relaxation rate associated with same. Methods of deuterating polymers are known in the art. For example, the deuteration of hydrocarbon polymers is described in U.S. Pat. Nos. 3,657,363, 3,966,781, and 4,914,160, the disclosures of which are hereby incorporated by reference herein. Typically, these methods use catalytic substitution of deuterons for protons. Preferred deuterated hydrocarbon polymers and copolymers include deuterated paraffins, polyolefins, and the like. Such polymers and copolymers and the like may also be cross-linked according to known methods.

It is further preferred that the polymer be substantially free of paramagnetic contaminants or impurities such as color centers, free electrons, colorants, other degrading fillers and the like. Any plasticizers or fillers used should be chosen to minimize any magnetic impurities contacting or positioned proximate to the hyperpolarized noble gas.

Alternatively, the first layer or contact surface can be formed with a high purity (and preferably non-magnetic) metal surface such as a metallic film. The high purity metal surface can provide advantageously low relaxivity/depolarization-resistant surfaces relative to hyperpolarized noble gases. Preferred embodiments will be discussed further below. Of course, the high purity metal film can be combined with the materials discussed above or can be used with other materials to form one or more layers to provide a surface or absorption region which is resistant to contact-induced depolarization interactions.

As noted above, any of these materials can be provided as a surface coating on an underlying substrate or formed as a material layer to define a polarization friendly contact surface. If used as a coating, the coating can be applied by any number of techniques as will be appreciated by those of skill in the art (e.g., by solution coating, chemical vapor deposition, fusion bonding, powder sintering and the like). Hydrocarbon grease can also be used as a coating. As noted above, the storage vessel or container can be rigid or resilient. Rigid containers can be formed of Pyrex™ glass, aluminum, plastic, PVC or the like. Resilient vessels are preferably formed as collapsible bags, preferably collapsible multi-layer bags comprising several secured material layers. The multiple layer configuration can employ material layers formed of different materials, i.e., the material layers can be selected and combined to provide a collapsible bag which is oxygen resistant, moisture resistant, puncture resistant, and which has a gas contacting surface which inhibits contact-induced depolarization. As used herein, the term "oxygen resistant" means that the bag is configured to inhibit the migration of oxygen into the gas holding portion of the bag. Preferably, the bag is configured to provide an oxygen leak rate or oxygen permeability rate of less than about 5×10$^{-6}$ amgt/min, more preferably less than 5.2×10$^{-7}$ amgt/min, and still more preferably less than about 1×10$^{-7}$ amgt/min at one atmosphere of pressure.

Containers

Figure 7:
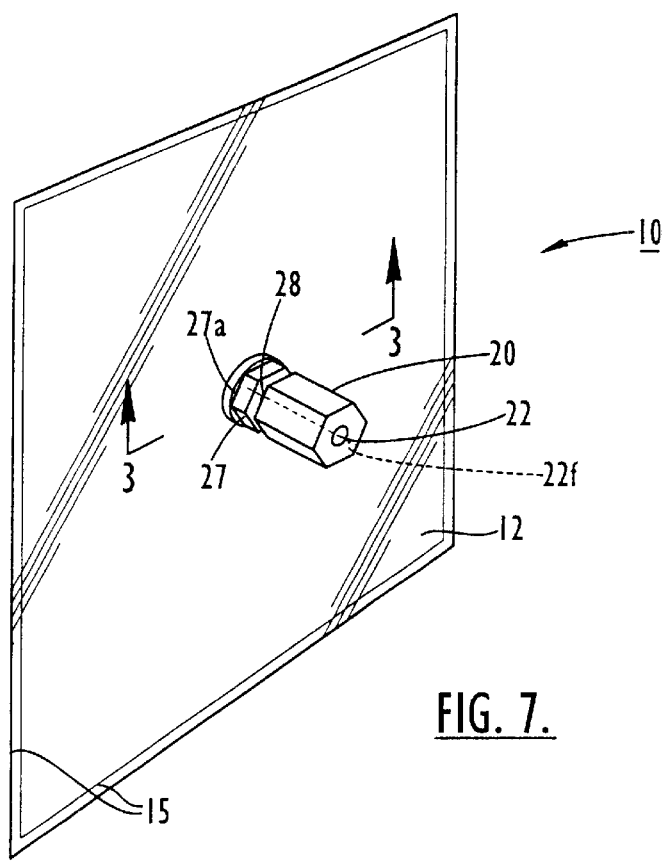
FIG. 7 is a perspective view of a hyperpolarized gas container according to one embodiment of the present invention in a deflated state.
Figure 8:
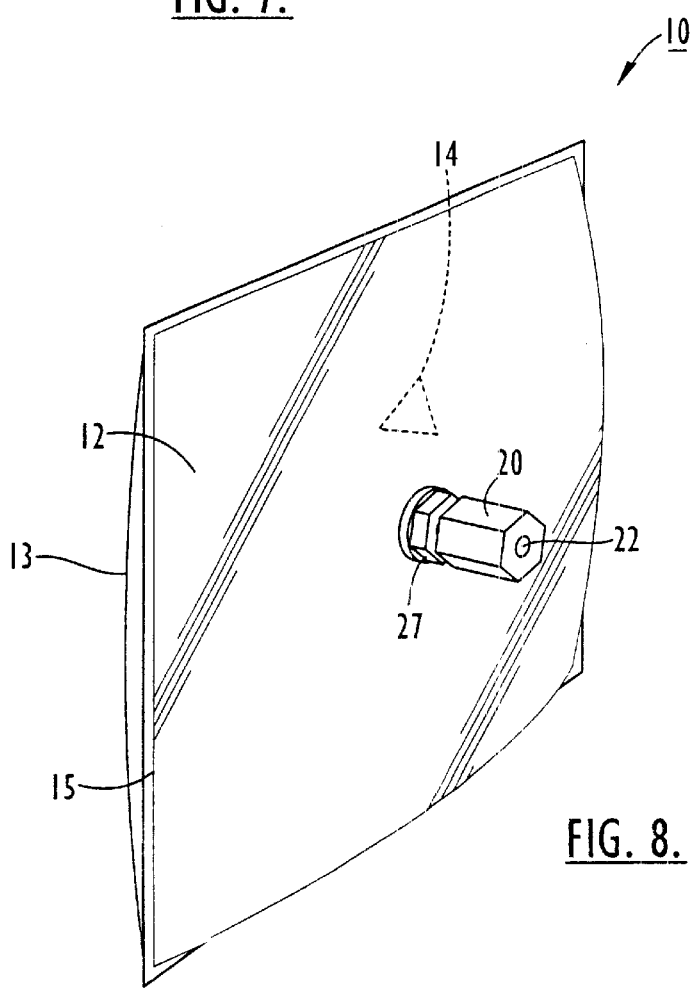
FIG. 8 is a perspective view of the container of FIG. 7, shown in an inflated state.

Turning again to the drawings, FIGS. 7 and 8 illustrate a preferred embodiment of a resilient container 10 for hyperpolarized gas according to the instant invention. FIG. 7 shows the container 10 in the collapsed (empty or void) position and FIG. 8 shows the container 10 when inflated (filled). As shown, the container 10 includes a front wall 12 and a rear wall 13 and a gas (or liquid) holding chamber 14 formed between the walls 12, 13. As shown, the walls 12, 13 are co-joined by a perimeter seal 15.

As shown in FIG. 7, in a preferred embodiment, the container 10 includes an outwardly extending port connector 20 in fluid communication with the port 22. The port connector 20 is preferably attached to the container 10 via a fitting 28. The fitting 28 can be heat sealed to the inside of the wall 12 to secure the fitting 28 to the inside of the container wall 12 in an airtight manner. Alternatively, as shown in FIG. 7, a gasket or O-ring 27a can be used to seal the fitting 28 to the container 10.

As shown in FIG. 9, the fitting 28 extends up through the container wall 12 and is secured against the outside of the container wall 12 via compression with a nut coupling member 27 and an intermediately positioned O-ring 27a. As is also shown, the nut coupling member 27 is positioned opposite the multi-layer container wall 12 and is configured such that it includes an aperture with internal threads which is positioned over and threadably mates with the external threads of the fitting 28c. Again, the seal provided by the nut coupling member 27, the associated O-ring 27a, and the fitting 28 are preferably configured to withstand up to about 3 atm of pressure and also are preferably configured to provide a vacuum-tight seal. In the embodiment shown in FIGS. 7 and 13, the port connector 20 is configured to define a portion of the fluid flow path 22f.

An alternate embodiment is shown in FIG. 9. In this embodiment, the port connector 20' is configured to function as a second top coupling nut which threadably engages with the fitting 28 separate from the nut coupling member 27. As shown, the port connector 20' includes an O-ring 20a positioned intermediate a bottom portion of the port connector 20b and a portion of the fitting 28b. As before, it is preferred that this seal between the fitting 28 and the port connector 20' also be configured in an airtight arrangement and be configured to withstand pressures up to about 3 atm (and is also preferably leak-tight at vacuum pressures used to condition the container, as will be discussed further below).

In a preferred embodiment, the container 10 includes a capillary stem 26s and a valve member 26. As shown in FIG. 9, the port connector 20' is configured to engage the capillary stem 26s which extends away from the chamber of the container 14 and which is in fluid communication with the valve member 26. The valve member 26 is operably associated with the chamber 14 such that it releasably controls the intake and release of the fluid. That is, in operation, the valve 26 is opened and hyperpolarized gas (or liquid) is directed through the outlet 29 through the body of the valve 26 and through the capillary stem 26s into the chamber 14, thereby forcing the container 10 to expand (FIG. 8) and capture the hyperpolarized gas (or liquid). The capillary stem 26s can be formed as an integral part of the valve member 26, or as a separate component. For example, the valve member 26 can include a body portion formed of glass such as Pyrex or the like, and the capillary stem 26s can be directly formed onto an end portion thereof as a glass such as Pyrex or an aluminosilicate, or other material to extend therefrom as a continuous body co-joined to the lower portion of the valve member 26. The valve illustrated in FIG. 9 includes a plug portion 26p with an O-ring 26o which longitudinally translates to engage with the lower nozzle end of the valve chamber 26n to close the flow path 22f in the valve closed position. In the reverse, the valve plug 26p moves away from the nozzle end 26n to allow the gas to flow through the port 22, the capillary stem 26s, and the valve body 26b and in (or out) the valve outlet 29.

Operationally, still referring to FIG. 9, the capillary stem 26s is configured such that a major portion of the hyperpolarized gas, once in the chamber 14, remains therein when the valve member 26 is closed. That is, the dimensions and shape of the capillary stem 26s are such that diffusion of the hyperpolarized gas away from the container chamber 14 is inhibited. Thus, the capillary stem 26s can reduce the amount of exposure for a major portion of the hyperpolarized gas with the valve 26 and any potentially depolarizing components operably associated therewith. In addition, the capillary stem 26s also provides a portion of the gas flow path 22f therethrough. As such, the capillary stem 26s includes an internal passage which is preferably sized and configured in a manner which inhibits the flow of gas from the chamber during storage or transport while also allowing the gas to exit the chamber 14 at its ultimate destination without undue or significant impedance.

Preferably, as discussed above the capillary stem 26s is operably associated with the valve member 26 and is configured to retain a major portion of the gas in the bag chamber 14, and away from the valve body 26b when the valve member 26 is closed. In the reverse, when the valve member 26 is opened, the gas exits the chamber 14 into the flow path 22f to the outlet 29. Thus, in operation, when the valve member 26 is closed, the capillary stem 26s helps keep a majority of the hyperpolarized gas away from the valve member 26 (such as retained at least below the O-ring in the nozzle end of the valve designated by the stepped down portion of the valve body in FIG. 9) to thereby inhibit any contact-induced depolarization which may be attributed thereto. In one embodiment, the capillary stem 26s has a length which is at least about 2.0 inches with a ⅛ inch inner diameter and a 0.2 inch outer diameter. For a 7×7 inch bag (or approximately one liter) container, this length is greater than about 20% the length or width of the container 10.

As shown in FIG. 9, the valve member 26 includes an externally accessible adjustment knob 26a which rotates to open and close the valve member 26. As is also shown, the valve member 26 includes a plurality of O-rings 26o therein. A suitable glass valve is available from Kimble Kontes Valves located in Vineland, N.J.

As is also shown in FIG. 9, the capillary stem 26s is positioned intermediate the valve member 26 and the container chamber 14 to inhibit the migration of the hyperpolarized substance into the valve member 26 to reduce the exposure to any potentially depolarizing materials therein (which potentially includes one or more of the O-rings 26o). Preferably, all sealing and structural materials associated with the container 10 and other container assembly components which come into contact with hyperpolarized gas are selected or formed of materials which are preferably substantially non-depolarizing.

Preferably, the capillary stem 26s is formed with a substantially rigid body. As used herein, the term "rigid" means that it can structurally help support the weight of a valve member 26 when assembled to the container 10 to minimize the stress/strain which may be introduced onto the juncture of the fitting 28. For example, the rigid body of the capillary stem 26s can be provided by a rigid substrate, such as a plastic, a PVC material, a glass, Pyrex, or aluminosilicate material, a metal, and the like. Of course, the hyperpolarized gas or fluid contacting surfaces of the capillary stem 26s are preferably formed with a material or coating which is substantially non-depolarizing to the hyperpolarized gas or liquid held therein (low relaxivity and or solubility for the hyperpolarized gas). It should also be noted, that, as shown, the capillary stem 26s is an elongated cylindrical stem, but other configurations are also possible. Preferably, whatever the configuration, the inner passage (shown as a diameter) of the capillary stem 26s is configured to inhibit or restrict the flow of fluid from the chamber of the bag 14 when the valve member 26 is closed.

Figure 17:
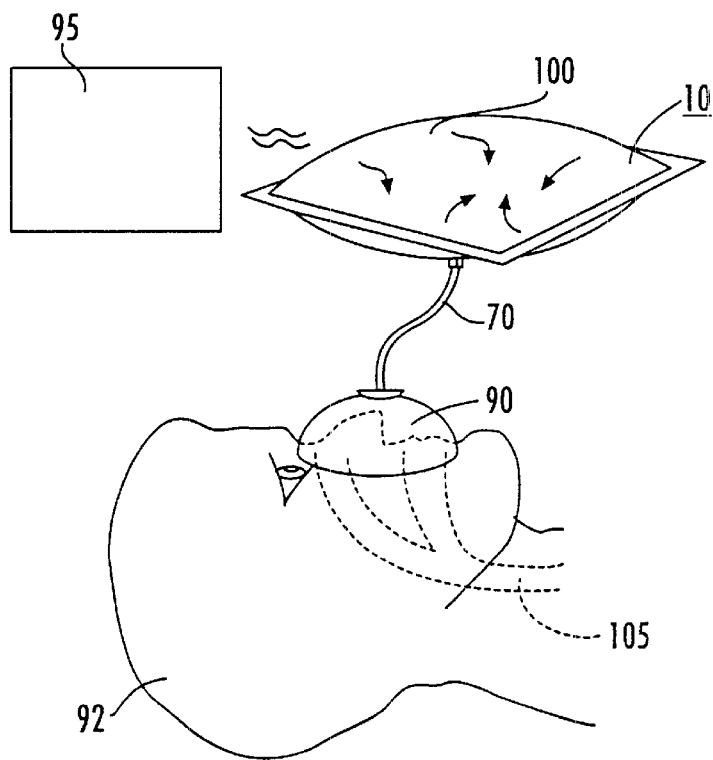
FIG. 17 is a schematic illustration of the resilient container of FIG. 13 shown attached to a user interface adapted to receive the container for delivering the hyperpolarized gas therein to the user according to one embodiment of the present invention.
Figure 18:
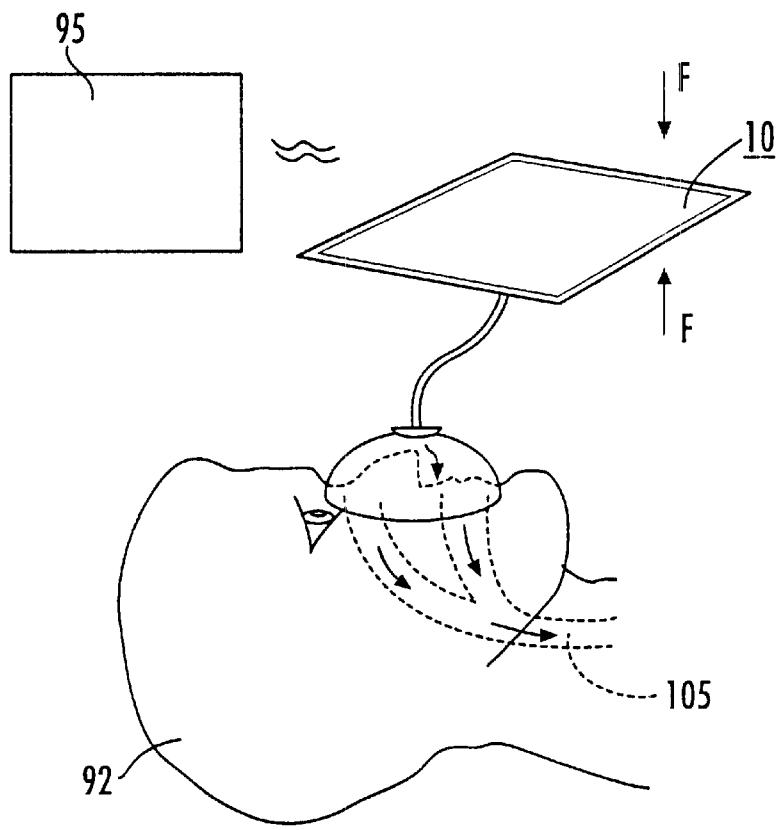
FIG. 18 shows the container of FIG. 17 in a deflated condition after forces on the container cause the hyperpolarized gas to exit the container and enter the target.
Figure 19:
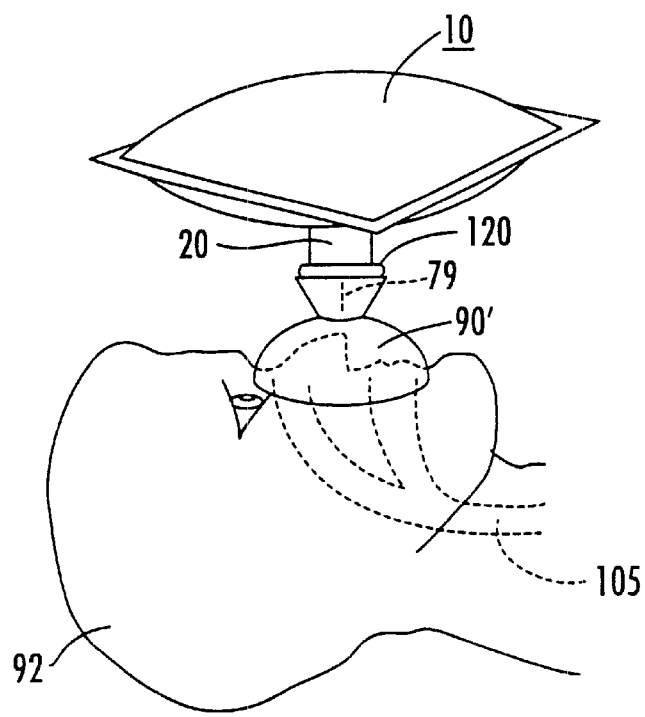
FIG. 19 is a schematic illustration of the container of FIG. 15 shown attached to a user interface according to one embodiment of the present invention.

Referring again to FIG. 9, the valve member 26 is configured with an end portion which holds the outlet 29 away from the capillary stem 26s which forms the hyperpolarized gas inlet and outlet port. Preferably, the outlet 29 is configured with a sealing means 25 which allows the container to mate and engage with an external device at the ultimate destination or delivery point (in an air tight manner) to facilitate the delivery of the gas or liquid without exposure to atmosphere. As shown, this sealing means 25 includes an O-ring 25a which is configured to sealably engage with the external device. In operation, the sealing means 25 compresses the O-ring 25a to matably engage with the delivery or input device (not shown). As such, the container chamber 14, the fitting 28, the capillary stem 26s, a portion of the valve member 26, and the end portion of the valve member 29 define the hyperpolarized fluid flow path 22f. Thus, in the embodiment shown in FIG. 9, when the valve member 26 is open, the fluid flow path 22f extends from the container chamber 14 through the capillary stem 26s to an external device or source such as a hyperpolarizer dispensing port (such as during filling) or patient delivery interface (such as at a gas delivery clinical use point). That is, a clinician or physician can merely turn the knob 26a to open the valve member 26 and compress the walls of the bag to release or expel the hyperpolarized gas from the chamber 14. In a preferred embodiment, as shown in FIGS. 17–19, the chamber 14 is engaged with a destination interface. As shown, the container 10, when compressed, expels the gas directly into a patient interface mask 90 so that a patient can inhale or breathe the gas therefrom.

Of course, other flow path configurations can be used (with and without the capillary stem 26s and/or valve member 26) such that the hyperpolarized fluid flow path 22f is defined by other components such as intermediate, distal, or proximate tubing or conduit (relative to the chamber of the bag). An example of the use of conduit 70 without a capillary stem 26s is illustrated in FIG. 17. For the conduit or tubing embodiment, various materials can be used for the conduit. An example of one suitable material alternative is polymer tubing attached to the fitting 28 and/or connector 20 and in fluid communication with the chamber 14. The tubing is formed such that at least the inner surface comprises a polarization friendly material with a suitable relaxivity or solubility value to provide a sufficiently long $T_1$ and the outer layer comprises a mechanically stable (i.e., self supporting), oxygen resistant flexible polymer matrix. Of course, depending on the material selection, the tubing can be formed as a unitary single layer body wherein the inner surface and outer layer material are the same, or the tubing can include a coated inner surface and a different material outer surface or wall layer.

Figure 21A:
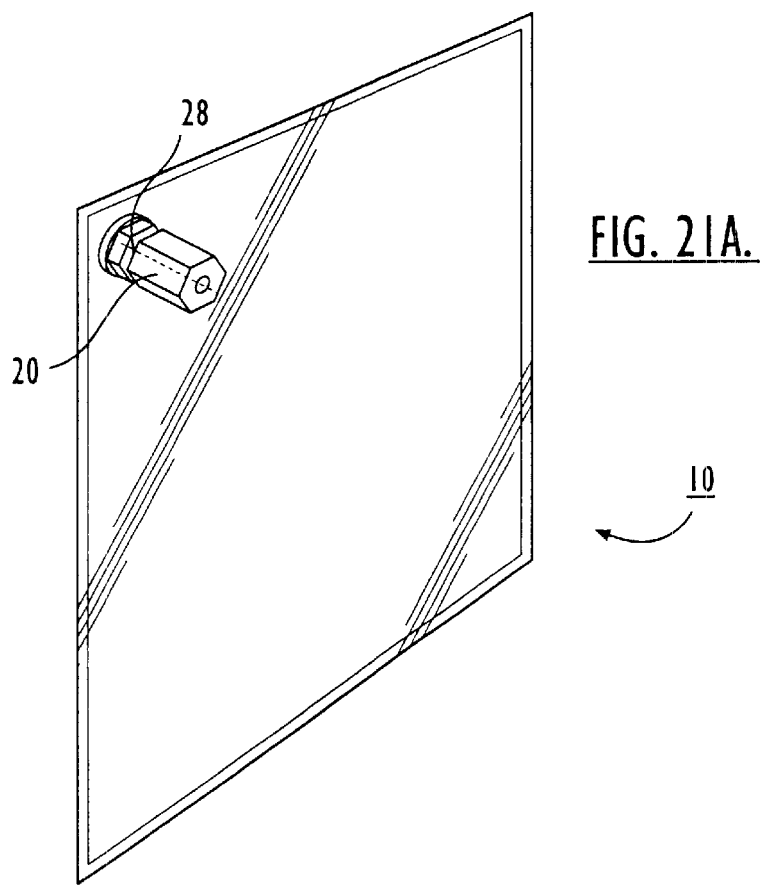
FIGS. 21A–21C are perspective views of an alternative embodiment of a container with a port isolation means according to the present invention.
Figure 21B:
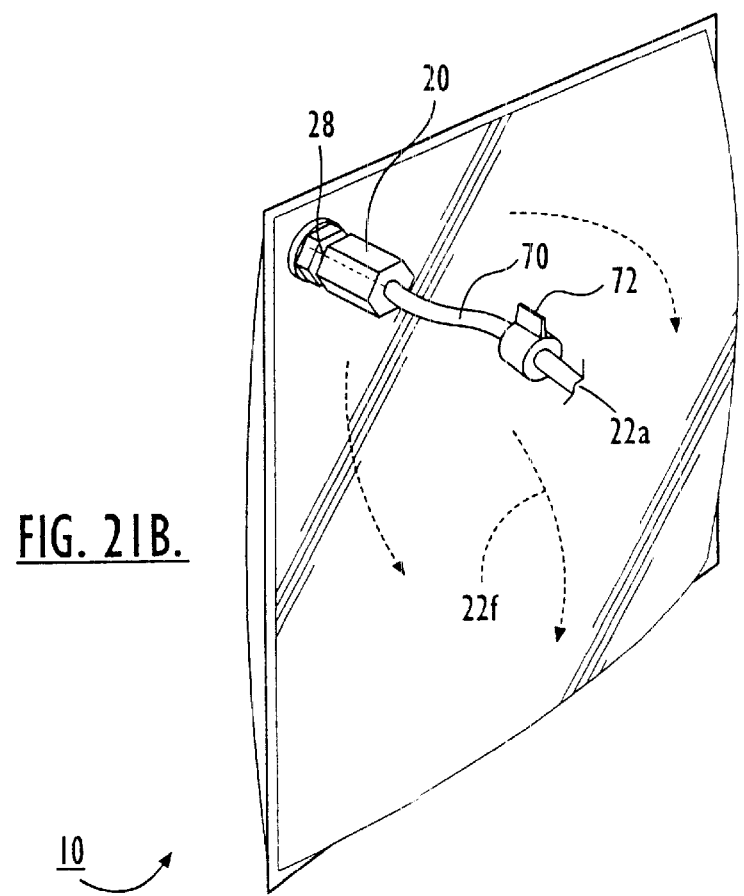
Figure 21C:
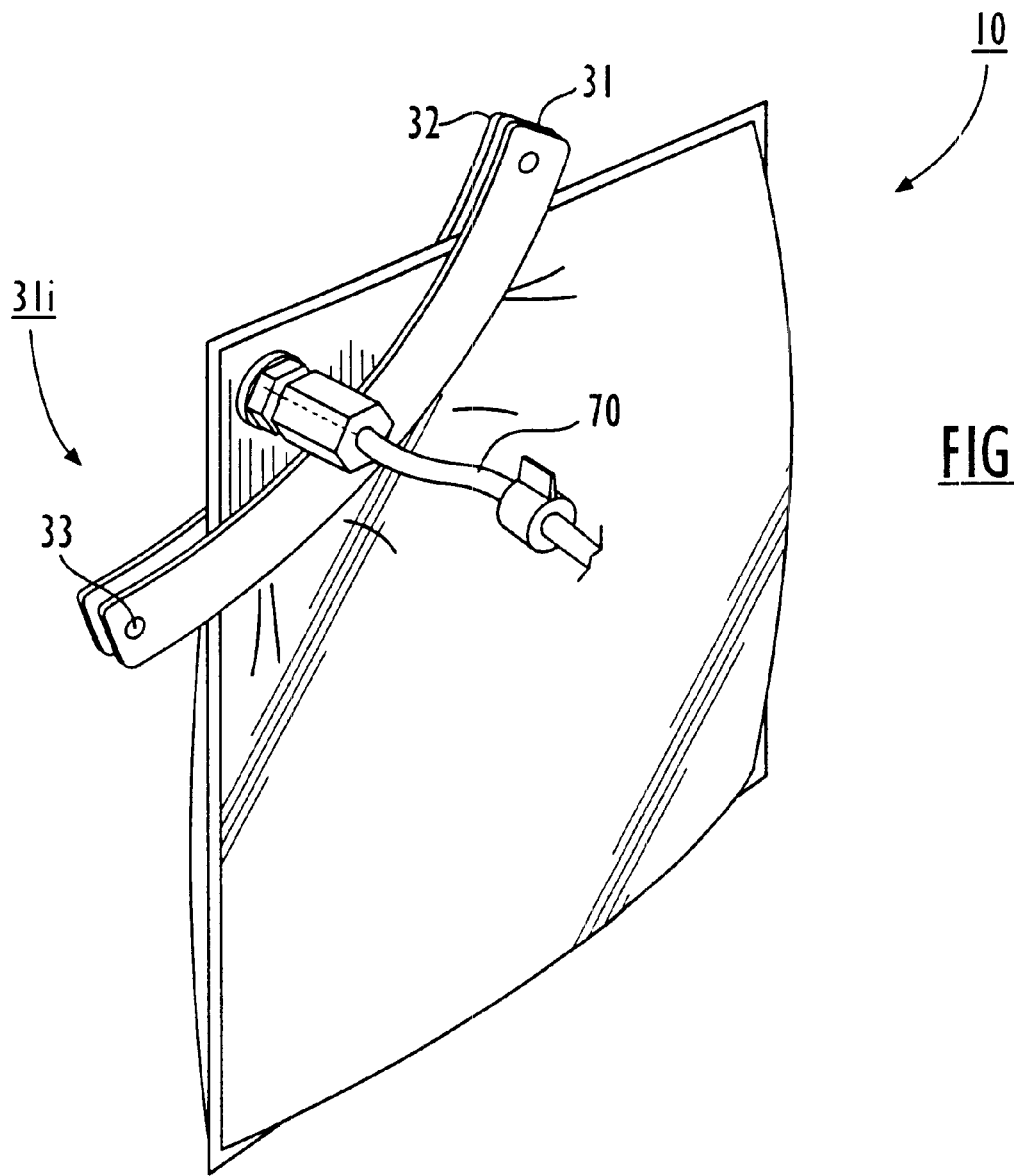

FIGS. 21A, 21B, and 21C illustrate yet another preferred embodiment of a container 10. As shown, this embodiment is similar to that shown in FIG. 7, except that the fitting 28 can be further isolated from the main volume of gas (or liquid) held in the chamber 14 as shown in FIG. 21B. As shown, the container is configured to position the port 22 at an edge portion of the container body. In addition, it is also preferred that an isolation means 31 is positioned intermediate the port and main volume of the chamber to isolate the port 22 and port fittings 28 or other components from the gas or liquid in the container during transport and storage. As such the gas or liquid's exposure to the port 22 or port fittings 28 is reduced. In operation, the container is in an unfilled (deflated position) as shown in FIG. 21A. Flexible tubing such as tygon® is attached to the container as shown in FIG. 21B. It is also preferred that the tubing be operably associated with a sealing means such as a clamp, valve or the like as discussed herein for other embodiments. As shown in FIG. 21B, a quantity of hyperpolarized gas or fluid is directed into the container through the aperture 22a as schematically indicated by the arrows. As shown in FIG. 21C, when the resilient container is sufficiently full (but below full capacity), an isolation means 31i is attached or formed onto the bag to pinch or enclose the bag portion with the port 22 and/or fitting 28 in a manner which will inhibit the contact of the main volume of hyperpolarized gas or liquid with this region of the bag or container. As shown, the isolation means 31i is a clamp having opposing clamping bars 31, 32 compressed together by fastener 33. Of course, other isolation means can also be used such as heat sealing, tying, restrictive (pinching) with bag configurations or holding fixtures and the like. For example, the bag container can be sized and configured with the port on an edge portion, preferably, proximate to a corner, and the container partially filled so that the corner can be folded against the body of the container and held in place simply by attaching a portion of the external wall to an opposing wall such as via an adhesive attachment means, velcro™, hook, and the like. The fold line acts to "pinch" off the main chamber of the container from the port (not shown) in a manner which is substantially air tight. Of course, a fold bar or other device can be used to facilitate a tight fold line between the port region and the major volume of the bag.

A multi-layer (3 ply) resilient container 10 having a capillary stem 26s and valve member 26, as shown in FIG. 9, can provide a corrected $T_1$ (taking into account the material properties alone) for hyperpolarized ³He gas of at least about 450 minutes (7.5 hours), and more preferably a corrected $T_1$ of at least about 600 minutes (10 hours) and an associated oxygen permeability rate of about $5.2 \times 10^{-7}$ amgt/min (at one atmosphere of pressure).

In a preferred embodiment, as shown in FIG. 12, the walls 12, 13 are configured with two layers 41, 44. The first layer 41 includes the inner contact surface 12a of the chamber 14 that holds and thus contacts the hyperpolarized gas. As such, the hyperpolarized noble gas is susceptible to contact-induced depolarization depending on the type of material and the depth of the material used to form this layer. Thus, this surface is preferably formed by a coating or a material layer with a sufficient thickness for preventing the hyperpolarized gas from sampling the underlying substrate. Also, the surface should have a low relaxivity relative to the hyperpolarized gas. As such, both the material and the thickness are chosen and configured to inhibit the surface-induced depolarization of the gas. As regards the thickness, it is preferred that the thickness be greater than the critical decay scale length $L_p$ and more preferably greater than a plurality of the decay length scale. For example, for ³He and HDPE, the critical length scale is about 8 μm so a preferred material layer depth is greater than about 16–20 μm.

Further, as regards the "low relaxivity", it is preferred that for ³He the material have a relaxivity value less than about 0.0013 cm/min and more preferably less than 0.0008 cm/min. For $^{129}$Xe, it is preferred that the material have a relaxivity value less than about 0.012 cm/min and more preferably less than about 0.0023 cm/min. "Reduced solubility" is meant to describe materials for which the hyperpolarized gas has a reduced solubility. Preferably, as regards $^{129}$Xe, the solubility is less than about 0.75, and more preferably less than about 0.4. For ³He, the solubility is preferably less than about 0.03, and more preferably less than about 0.01.

The second layer 44 includes the external surface 12b that is exposed to air which includes components which can be potentially degrading to the hyperpolarized gas in the chamber. For example, as discussed above, paramagnetic oxygen can cause depolarization of the gas if it migrates into the contact surface 12a or the chamber 14. As such, it is preferred that the second layer 44 be configured to suppress oxygen migration. The second layer 44 can be formed as an oxygen-resistant substrate, a metal layer, or metallized deposit or coating formed over another layer. Preferably, the second layer 44 (alone or in combination with other layers) prevents de-magnetizing amounts of $O_2$ from entering into the chamber at a rate greater than $5 \times 10^{-6}$ amgt/min, and more preferably at a rate which is less than about $1 \times 10^{-7}$ amgt/min. More preferably, for a desired $T_1$ of about 24 hours and after 24 hours of permeation, it is preferred that the $O_2$ concentration be less than about $2.6 \times 10^{-5}$ amgt. Thus, at 1 atm, for a 1 liter bag, it is preferred that the container be configured to maintain the $O_2$ concentration in the chamber below 0.003% of the total gas concentration. Of course, the second layer can be alternatively chosen or configured to shield other environmental contaminants such as moisture. For example, in this embodiment, a first layer may have a very low permeability for $O_2$ but may be sensitive to moisture. The second layer 44 can be configured with a protective polyethylene coating to compensate for this property and provide an improved $T_1$ container.

In yet another alternative embodiment, the inner surface 12a can be configured as a high purity (non-magnetic) metal film applied to an underlying substrate, polymer, or other container material. High purity metal surfaces can provide even better protection against depolarization relative to other surfaces. Because the hyperpolarized gas contacts the metal, the underlying material is not required to have a low solubility for the hyperpolarized gas. In a preferred embodiment, the container is resiliently configured as a collapsible bag with the inner surface 12a formed from a high purity metal film (preferably a thickness within the range of about 10 nm to about 10 microns). As such, in this embodiment, the first layer 41 is the metallized layer and can provide the oxygen resistance/shield as well as protection against contact depolarization. Preferred metals include those that are substantially paramagnetically pure (i.e., they do not introduce magnetic moments) and resistant to contact depolarization of the hyperpolarized gases. Stated differently, the metal used should be chosen to minimize the adsorption time of the gas on the metal surface, i.e., such that the noble gas has a low adsorption energy on the metal surface. Examples of suitable materials include, but are not limited to, aluminum, gold, silver, indium, beryllium copper, copper, and mixtures and blends thereof. As used herein, "high purity" includes materials which have less than 1 ppm ferrous or paramagnetic impurities and more preferably less than 1 ppb ferrous or paramagnetic impurities.

In an additional embodiment, the inner surface 12a can be formed as a hybrid surface (a blend or side by side disposition of high purity metal film and polymer) or as a high purity metal formed over a polymer substrate. As such, a metal film can be layered over a polymer with good relaxivity properties to compensate for cracks or gaps which may develop in the metal film layer.

In another preferred embodiment, as shown in FIG. 12, the inner surface 12a is formed directly by the inner wall of a polymer bag and the outer or intermediate surface is formed by a metallized coating or material positioned over and directly contacting the polymer bag. However, as illustrated in FIGS. 10 and 11, intermediate layers 42, 43 positioned between the inner layer 41 and outer layer 44 can also be used. For example, in a preferred embodiment, the container has three layers 41,42,44. The first layer 41 is 0.004" linear LDPE; the second layer 42 is 0.0005" aluminum foil, and the third layer 44 is 48 gauge polyester. Advantageously, the first LDPE layer provides a polarization-friendly surface with a relatively long $T_1$, the second aluminum foil layer inhibits oxygen permeation, and the polyester layer provides strength and puncture resistance. The outer layers 41 and 44 are secured to the middle layer 42 with urethane adhesive. Typically the layers are cemented or bonded together but other joining or securing means can be used as will be recognized by those of skill in the art. A container 10 with this three-layer configuration has been observed to have a corrected $T_1$ (due to material only) for $^3$He of about 490 minutes (over 8 hours) and an oxygen leak rate of about $3.9 \times 10^{-5}$ amgt/min. This $T_1$ is contrast to that obtained in the single layer bag used in the past. For example, the $T_1$ for $^3$He in a conventional 1 liter single layer Tedlar bag (pre-conditioned such as described hereinbelow) has been estimated to be under about 4 hours.

In FIG. 10, the container 10 has four layers 41, 42, 43, 44. As shown, the inner layer 41 is not a coating but is defined by the expandable polymer (or modified polymer) bag having a thickness sufficient to inhibit contact depolarization. In this embodiment the intermediate layers can be formed from any number of alternative materials, preferably resilient materials so as to contract and expand with the inner layer 41. In a preferred embodiment, the inner layer 41 is about 0.0025"(inches) of linear LDPE (LLDPE); the second layer 42 is about 0.003 inches of Al; the third layer 43 is 71b PE, and the outer layer 44 is 48 gauge PET. A bag container with this multi-layer configuration has been shown to have a corrected $T_1$ (due to material alone) of about 14 hours and an oxygen leak rate substantially less than about $3 \times 10^{-8}$ amgt/min at one atmosphere.

In one embodiment (not shown) a bag with five layers is used: the first layer is 35 μm of HDPE; the second layer 42 is 35 μm of polyamide; the third layer 43 is 1 μm of aluminum; the fourth layer 44 is 35 μm of polyvinylidene chloride; and the fifth layer (not shown) is 35 μm of polyester. Advantageously, the multiple layers can provide additional strength and/or puncture and pressure resistance. Of course, alternative materials and numbers of layers can also be employed according to the present invention.

In one embodiment (not shown), a coating can be placed on the inner surface 12a of the polymer bag to define the proper depth of the contact layer either alone or in combination with the thickness of the polymer bag. Of course, the two layers can be formed as one layer if the container material employed has a low-relaxivity for the hyperpolarized gas and if the material is sufficiently impermeable to environmental contaminants such as 2. Examples of such materials include but are not limited to PET (polyethylene terphthalate), PVDC (polyvinylidene dichloride), cellophane and polyacrylonitrile.

As shown in FIGS. 9 and 13–15, the container 10 also includes a sealing means operably associated with the entry port 22 and used to capture the hyperpolarized gas within the chamber 30. Generally described, the sealing means closes off the passage 22a in communication with the bag entry port 22 (FIG. 7), thereby retaining the hyperpolarized gas substantially within the chamber 14 of the container. The sealing means can be configured in a number of ways, either with valves integrated with the bag (FIG. 9) and or with clamps or other devices which are positioned onto the flow path of the container. In the configuration shown in FIG. 13, the coupling member 20 includes a conduit 70 extending outwardly therefrom in the flow path, and the sealing means is a clamp or heat seal applied to the conduit. Examples of suitable sealing means include, but are not limited to, a clamp 72 (FIG. 13) a heat seal 74 (FIG. 14) and a membrane seal 76 (FIG. 15). Alternatively, the valve 26 (FIG. 9), a stop-cock, and other fittings and/or seals (gaskets, hydrocarbon grease, O-rings) (not shown) can be used to control the release of the hyperpolarized gas. Preferably, care is taken to insure all fittings, seals, and the like which contact the hyperpolarized gas or which are located relatively near thereto are manufactured from materials which are friendly to polarization or which do not substantially degrade the polarized state of the hyperpolarized gas. For example, as noted above, many commercially available seals include fluoropolymers or fillers and the like which are not particularly good for the preservation of $^3$He hyperpolarized gases because of the solubility of the material with the hyperpolarized gas.

Inasmuch as many common gasket materials are fluoropolymers or contain undesirable fillers, they can potentially have a substantially depolarizing effect on the gas. This can be especially acute with respect to $^3$He. This can be attributed to a relatively high solubility of helium in most fluoropolymers due to the larger void space in the polymer attributable to the large fluorine atoms. Indeed, preliminary tests indicate that materials of common O-rings (such as Viton™, Kel-F™, ethylenepropylene, Buna-N™, and silicone) exhibit far worse relaxation properties than would be expected from the relaxation rate of pure polymers. Most conventional O-rings are so depolarizing that they can dominate the relaxation of an entire hyperpolarized gas chamber. Indeed, commercial ethylene propylene O-rings exhibit ⅓–½ the relaxation time compared to pure LDPE with $^{129}$Xe. The faster relaxation rate can be explained because magnetic impurities in the O-rings can be introduced by such things as colorants and fillers and the like. Therefore, it is preferred that the containers of the present invention employ seals, O-rings, gaskets and the like with substantially pure (substantially without magnetic impurities) hydrocarbon materials such as those containing polyolefins. Examples of suitable polyolefins include polyethylene, polypropylene, copolymers and blends thereof which have been modified to minimize the amount of magnetically impure fillers used therein. Additional suitable seals include hydrocarbon grease and hydrocarbon gaskets and O-rings made from polyethylene and the like. Thus, if a valve is used to contain the gas in the chamber 30, it is preferably configured with a magnetically pure (at least the surface) O-ring and/or with hydrocarbon grease. Of course, because fillers and plasticizers are employed, then it is preferred that they be selected to minimize the magnetic impurities such as substantially pure carbon black.

In an alternative embodiment, the O-ring seal can be configured with the exposed surface coated with a high purity metal as discussed for the container surface. Similarly, the O-ring or seal can be coated or formed with an outer exposed layer of a polymer at least "$L_p$" thick. For example, a layer of pure polyethylene can be positioned over a commercially available O-ring. One preferred commercially available O-ring material for $^{129}$Xe is a Teflon™ coated rubber O-ring or a low-relaxivity polymer as discussed above. The void spaces in Teflon™, although a fluoropolymer, do not affect $^{129}$Xe as much as it does $^3$He because $^{129}$Xe is much larger than fluorine, which is much larger than $^3$He. As discussed previously, fluoropolymers can be used as seals with $^{129}$Xe but are not preferable for use with arrangements where the seal may contact the hyperpolarized $^3$He.

In operation, after delivery to a use site, the technician or patient can open the valve member 26 (FIG. 9) and breathe in, or halt the flow by placing a temporary clamp 72 on the conduit 20 (FIG. 13). FIGS. 13 and 14 illustrate preferred embodiments of a seal arrangement used to ship or store the filled container. Each acts to seal the fluid passage 22a by pinching the conduit 70 shut in at least one position therealong. FIG. 13 shows the use of an external clamp 72 and FIG. 14 shows the use of a redundant heat seal 74. In operation, each is easily employed with little impact on the polarization of the gas in the container 10. For example, for the embodiment shown in FIG. 14, after the container 10 is filled with hyperpolarized gas, an in-process clamp (not shown) is inserted over the conduit 70 such that it closes off the passage 22a. Heat is applied to the conduit 70 as the conduit wall is collapsed to provide a heat seal 74 to at least one side of the in-process clamp. The bag is then ready to transport. Once at the desired delivery location site, the heat seal 74 can be cut away and a temporary clamp can be placed on the conduit 70. As shown in FIG. 17, the conduit 70 can be directly engaged with a breathing apparatus or patient interface 90. As illustrated in FIG. 18, the hyperpolarized gas can be forced out of the bag and into the interface 90 such as by externally depressing/compressing the walls of the container 10. Alternatively, the patient 92 can simply inhale thereby directing the gas 100 into the inhalation pathway 105.

Turning now to FIG. 15, in another embodiment, a membrane seal 76 is positioned directly over the external portion of the entry port 22. The membrane seal 76 can be attached by heat, or an anchoring member such as a polymer washer threadably attached over the peripheral portion of the coupling member 22, preferably leaving the central portion 76a externally accessible. In this embodiment, as shown in FIG. 19, the container 10 can be transported to the use site and inserted directly into a patient interface 90'. Preferably, the membrane seal 76 is inserted into the interface 90' such that it is positioned internal to the air tight coupling provided by the joint 130 between the coupling member 20 and the interface 90'. Advantageously, the interface 90' can include a puncture 79 recessed within the receiving area to open the central portion of the membrane seal 76 after the coupling member 20 forms the external joint 120 such that the container is sealed to the interface 90'. This allows the gas in the container to be easily released and directed to the patient. The gas can be easily extracted or forced out of the container 10 by depressing the walls 12, 13 of the container 10 or via inhalation. Advantageously, such a configuration removes the requirement for relatively complex or sophisticated gas extraction mechanisms and also reduces the amount of physical manipulation and/or interfaces required to deliver the gas to the subject.

Figure 16:
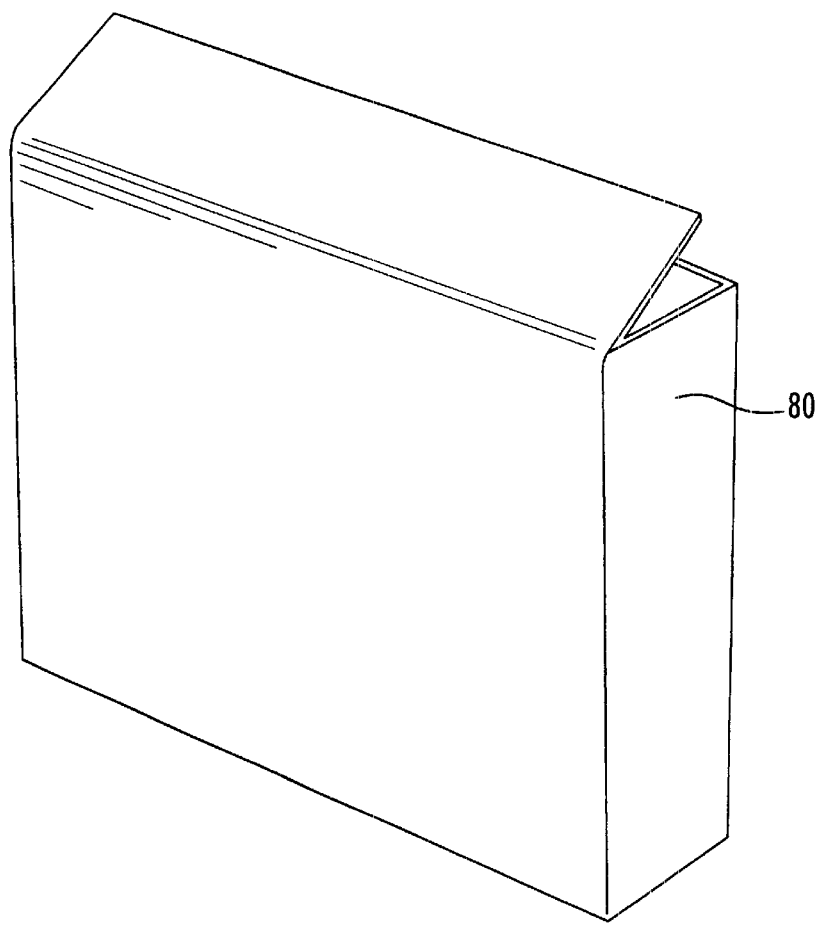
FIG. 16 is a side perspective view of a shielded shipping receptacle configured to receive the container according to one embodiment of the present invention.

As shown in FIG. 16, a shipping box 80 is preferably used to hold the bag 10 during transport. This can help protect the bag from physical hazards. In addition, it is preferred that the box 80 include magnet means to provide a desired static magnetic (substantially homogeneous) field around the hyperpolarized gas. In addition, or alternatively, the box 80 can be configured to form a shield from undesirable stray magnetic fields as will be discussed further below.

In summary, the present invention provides containers which improve on the relaxation time of the hyperpolarized gas. Preferably, the container is sized and configured and the contact surface formed from a suitable material such that the hyperpolarized gas in the container has a relaxation time greater than about 6 hours and more preferable greater than about 20 hours for $^3$He. Similarly, the container is preferably sized and configured such and the contact surfaces formed from a suitable material that the $^{129}$Xe hyperpolarized gas in the container has a relaxation time greater than about 4 hours, preferably more than about 6 hours, and more preferably greater than about 8 hours.

Shielding

The present invention recognizes that unless special precautions are taken, relaxation due to external magnetic fields (static and/or time dependent) can dominate all other relaxation mechanisms. Both gradients in the static field and (low frequency) oscillating magnetic fields experienced by the hyperpolarized gas can cause significant relaxation.

Advantageously, an (externally) applied substantially static magnetic holding field "$B_H$" can substantially protect the hyperpolarized gas from depolarizing effects attributed to one or more of the EMI and gradient fields during transport. The instant invention employs a magnetic holding field which raises the Larmor frequency of the hyperpolarized gas above the region of noise (1/f), i.e. the region where the intensity of ambient electromagnetic noise is typically high (this noise is typically under about 5 kHz). Further, a magnetic holding field is also preferably selected such that it raises the frequency of the hyperpolarized gas to a level which is above those frequencies associated with large acoustic vibrations (these acoustic vibrations are typically less than about 20 kHz). As will be discussed below, the increased frequency associated with the applied magnetic holding field advantageously allows a transport unit (FIG. 16) to have greater electromagnetic shielding effectiveness for a given housing thickness (the housing used to hold the hyperpolarized gas therein during transport and/or storage). The skin depth "δ" of a conductive shielding material is inversely proportional to the square root of the frequency. Thus, at 25 kHz, an exemplary skin depth for aluminum is about 0.5 mm, as compared to about 2.0 mm at 1.6 kHz.

Preferably, the magnetic holding field of the instant invention is selected so that any external field-related fluctuations are small in magnitude compared to the field strength of the holding field; in this way the holding field can minimize the hyperpolarized gas's response to unpredictable external static field gradient-induced relaxation. This can be accomplished by applying to the hyperpolarized gas a proximately positioned magnetic holding field which is sufficiently strong and homogeneous so that it minimizes the unpredictable static field-related relaxation during transport and storage. A sufficiently homogeneous holding field preferably includes (but is not limited to) a magnetic holding field which has homogeneity which is on the order of about at least $10^{-3}$ cm$^{-1}$ over the central part of the holding field (i.e., the part in which the gas resides). More preferably, the magnetic holding field homogeneity is about at least $5 \times 10^4$ cm$^{-1}$. Further, the magnetic holding field should be positioned, sized, and configured relative to the hyperpolarized gas such that it also minimizes the EMI or oscillating magnetic field depolarization effects. The depolarizing effect of EMI is preferably (substantially) diminished by applying the magnetic holding field ($B_H$) proximate to the gas so that the resonant frequency of the hyperpolarized gas is preferably above or outside the bandwidth of prevalent time-dependent fields produced by electrically powered or supplied sources.

Alternatively, or additionally, the external interference can be shielded by positioning a substantially continuous shield or shipping container having at least one layer formed of a conductive material such as metal around the hyperpolarized gas in the container. The preferred shielding thickness is related to the spatial decay constant of an electromagnetic wave or skin depth δ. The skin depth δ at an angular frequency ω is given by $\delta = c/(2\pi\mu\sigma\omega)^{1/2}$, where $\mu$ is the magnetic permeability and σ is the electrical conductivity of the material. At these frequencies, the Larmor radiation wavelength is long (~10 km), and is much larger than the container size. The shielding effectiveness is therefore dependent upon the container geometry as well as the shielding thickness. For a thin spherical conductor of radius a and thickness t, the shielding factor for wavelengths λ>>a is given approximately by $$F = (1 + (2at/3\delta^2)^2)^{1/2}$$

Interestingly, the shielding effectiveness increases as the size (radius) of the shield is increased. It is therefore preferred that a metallic enclosure used to shield or surround the hyperpolarized gas be configured to define an internal volume which is sufficient to provide increased shielding effectiveness. Stated differently, it is preferred that the walls of the enclosure are spaced apart a predetermined distance relative to the position of the gas container.

Alternatively, or additionally, a transport unit can be configured with at least one layer formed from about 0.5 mm thick of magnetically permeable material, such as ultra low carbon steel soft iron, or mu-metals (by virtue of their greater magnetic permeability). However, these materials may significantly influence the static magnetic field and must be designed accordingly not to affect the homogeneity adversely.

Irrespective of the skin depth of the materials (types of materials and number of layers) used to form a shipping container enclosure, application of a homogeneous magnetic holding field proximate to the hyperpolarized gas can help minimize the gas depolarization by virtue of decreasing the skin depth δ, which is inversely proportional to the square root of the frequency. Further, it helps by pushing the resonant frequency of the gas outside the bandwidth of common AC fields. It is preferred that the resonant frequency of the hyperpolarized gas be raised such that it is above about 10 kHz, and more preferably be raised such that it is between about 20–30 kHz. Stated differently, it is preferred that for shielding, the applied magnetic holding field have a field strength of about 2 to 35 gauss. It is more preferred that for $^{129}$Xe, the magnetic holding field is preferably at least about 20 Gauss; and for $^3$He, the magnetic holding field is preferably at least about 7 Gauss. See co-pending and co-assigned provisional U.S. patent application Ser. No. 60/121,315 for additional shielding method details and preferred transport unit configurations. The contents of this document are hereby incorporated by reference as if recited in full herein.

Preconditioning the Container

Preferably, due to susceptibility of the hyperpolarized to paramagnetic oxygen as noted above, the storage container 10 is preconditioned to remove contaminants. That is, it is processed to reduce or remove the paramagnetic gases such as oxygen from within the chamber and container walls. For containers made with rigid substrates, such as Pyrex™, UHV vacuum pumps can be connected to the container to extract the oxygen. However, a roughing pump can also be used which is typically cheaper and easier than the UHV vacuum pump based process for both resilient and non-resilient containers. Preferably, the bag is processed with several purge/pump cycles, e.g., pumping at or below 20 mtorr for one minute, and then directing clean buffer gas (such as Grade 5 or better nitrogen) into the container at a pressure of about one atm or until the bag is substantially inflated. The oxygen partial pressure is then reduced in the container. This can be done with a vacuum but it is preferred that it be done with nitrogen. Once the oxygen realizes the partial pressure imbalance across the container walls, it will outgas to re-establish equilibrium. Stated differently, the oxygen in the container walls is outgassed by decreasing the partial pressure inside the container chamber. Typical oxygen solubilities are on the order of 0.01–0.05; thus, 95–99% of the oxygen trapped in the walls will transition to a gas phase. Prior to use or filling, the container is evacuated, thus harmlessly removing the gaseous oxygen. Unlike conventional rigid containers, polymer bag containers can continue to outgas (trapped gases can migrate to the chamber because of pressure differentials between the outer surface and the inner surface) even after the initial purge and pump cycles. Thus, care should be taken to minimize this behavior especially when the final filling is not temporally performed with the preconditioning of the container. Preferably, a quantity of clean filler gas (such as Grade 5) is directed into the bag (to substantially equalize the pressure between the chamber and ambient conditions) and sealed for storage in order to minimize the amount of further outgassing that may occur when the bag is stored and exposed to ambient conditions. This should substantially stabilize or minimize any further outgassing of the polymer or container wall materials. In any event, the filler gas is preferably removed (evacuated) prior to final filling with the hyperpolarized gas. Advantageously, the container of the instant invention can be economically reprocessed (purged, cleaned, etc.) and reused to ship additional quantities of hyperpolarized gases.

It is also preferred that the container or bag be sterilized prior to introducing the hyperpolarized product therein. As used herein the term "sterilized" includes cleaning containers and contact surfaces such that the container is sufficiently clean to inhibit contamination of the product such that it is suitable for medical and medicinal purposes. In this way, the sterilized container allows for a substantially sterile and non-toxic hyperpolarized product to be delivered for in vivo introduction into the patient. Suitable sterilization and cleaning methods are well known to those of skill in the art.

Measuring Gas Solubility in a Polymer or Liquid

In the past, measuring gas solubilities of most polymers has been time consuming and difficult, and in the case of helium, usually inaccurate. However, as discussed above, the hyperpolarized gas relaxation time, $T_1$, is now determined to be proportional to gas solubility. Advantageously, due to the recognition and determination of the relationships discussed above, hyperpolarized noble gases such as $^3$He and $^{129}$Xe can be used to determine or measure the gas solubility in a polymer or liquid. This information can be valuable for quickly assessing the structures of the polymer. In addition, a given polymer sample can be evaluated using both $^{129}$Xe and $^3$He gases, as each can give complimentary information. For example, $^3$He will sample a greater depth of the polymer based on its greater diffusion coefficients.

Figure 20:
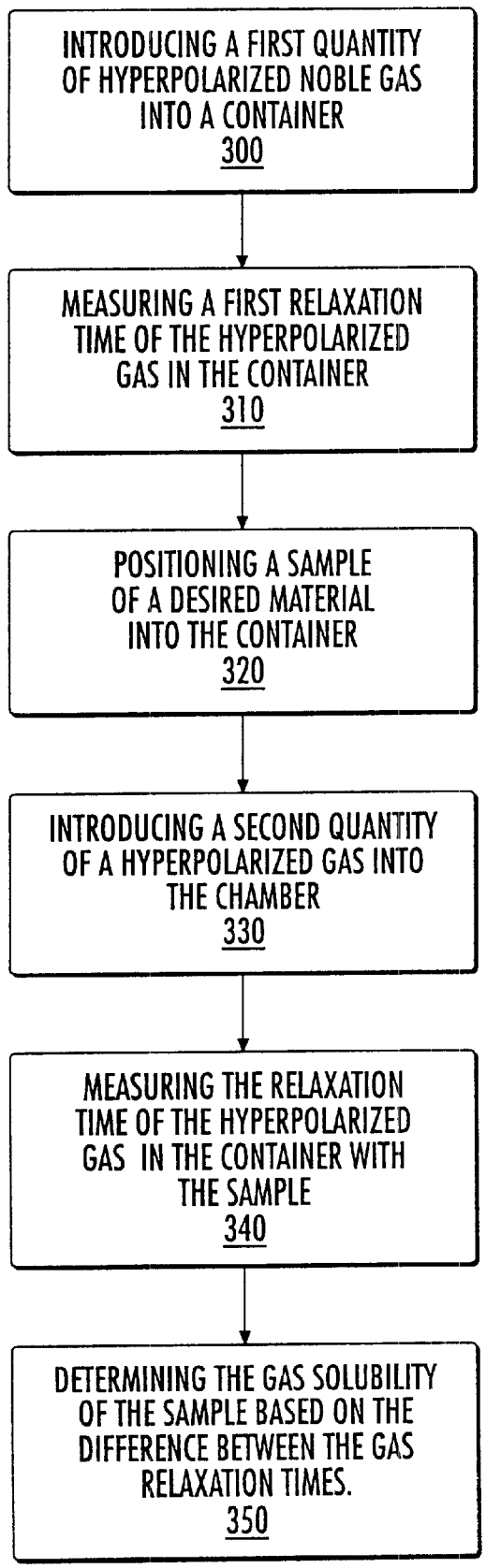
FIG. 20 is a block diagram of a method for determining gas solubility in a polymer according to one embodiment of the present invention.

Preferably, as shown in FIG. 20, a first quantity of a hyperpolarized gas is introduced into a container (Block 300). A first relaxation time is measured of the hyperpolarized gas in the container (Block 310). A selected material sample is positioned in the container (Block 320). A second quantity of a hyperpolarized noble gas is introduced into the container (Block 330). A second relaxation time is measured associated with the sample and the gas in the container (Block 340). The gas solubility is determined based on the difference between the two relaxation times (Block 350). Preferably this is determined according to equation (2.23c). The material sample can be a physical or solid sample or a liquid as described above.

Although the sample used above was a geometrically fixed polymer sample, the method can also be used to determine gas solubilities in liquids or fluids. For example, instead of placing a polymer sample into the chamber, a liquid can be introduced. The liquid will preferably be introduced in a quantity which is less than the free volume of the chamber as it will conform to the shape of the chamber to define an associated volume and surface area. The polarized gas can then be directed into the chamber with the liquid and the relaxation rate determined due to the specific liquid. This can be especially helpful in formulating carrier substances for injection formulations of hyperpolarized $^{129}$Xe and $^3$He.

EXAMPLES

In the examples provided below, the polymer contact surface is assumed to be present at a depth corresponding to a plurality of critical length scales as discussed above.

EXAMPLE 1

$^3$He LDPE/HDPE Bag

An exemplary one liter patient delivery bag, such as is shown in FIG. 7, is a 7 inch×7 inch square. The expected $T_1$ for $^3$He can be determined using (Equation 2.4) and the theoretical relaxivity of LDPE for $^3$He quoted in Table 4.3. The associated area (A=2*18 cm*18 cm) is 648 cm$^2$, the volume is 1000 cubic centimeters, and the relaxivity is 0.0012 cm/min. Equation 2.4 leads to a $T_1$ of about 1286 min or 21.4 hours for an LDPE bag configured and sized as noted above (absent other relaxation mechanisms). For a bag made of HDPE, which has a lower relaxivity value of about 0.0008 cm/min (attributed to the lower $^3$He solubility), the $T_1$ is estimated at 32 hours. In deuterated HDPE, the $T_1$ is expected to be about 132 hours.

EXAMPLE 2

$^{129}$Xe LDPE/Nylon Bag

The same 1 liter LDPE patient delivery bag as described in Example 1 contains hyperpolarized $^{129}$Xe. Volume and surface area are the same but the theoretical relaxivity is 0.0419 cm/min (Table 4.2) for $^{129}$Xe on LDPE. The relaxivity is much higher because of the higher solubility of $^{129}$Xe in LDPE compared to He ($S_{Xe}$=0.68 vs $S_{He}$=0.006). For this configuration, $T_1$ is estimated at 36.8 minutes. Similarly, for the measured relaxivity for Nylon-6 of 0.0104 cm/min, predict $T_1$ is predicted to be about 148 min or about 2.4 hours. This value is close to what has been measured for the presently used Tedlar™ bags.

EXAMPLE 3

Metal Film Surface

In this example, metal film coatings are used as the contact surface. The 7"×7" square bag described in Example 1 is employed but coated or formed with high purity aluminum on its internal contact surface (the surface in contact with the hyperpolarized gas). The relaxivity of high purity aluminum for $^{129}$Xe has been recently measured to be about 0.00225 cm/min. (One readily available material suitable for use is Reynold's™ heavy duty freezer foil). Doing the calculation, one can obtain a container with an extended $T_1$ for xenon of about 11.43 hours. This is a great improvement in $T_1$ for Xe. Similarly, the use of such metal film surfaces for $^3$He can generate $T_1$'s in the range of thousands of hours (the container no longer being a limiting factor as these $T_1$'s are above the theoretical collisional relaxation time described above). Metals other than aluminum which can be used include indium, gold, zinc, tin, copper, bismuth, silver, niobium, and oxides thereof. Preferably, "high purity" metals are employed (i.e., metals which are substantially free of paramagnetic or ferrous impurities) because even minute amounts of undesirable materials or contaminants can degrade the surface. For example, another high purity aluminum sample tested had a relaxivity of about 0.049 cm/min, a full 22 times worse than the sample quoted above. This is most likely due to the presence of ferrous or paramagnetic impurities such as iron, nickel, cobalt, chromium and the like. Preferably, the metal is chosen such that it is well below 1 ppm in ferrous or paramagnetic impurity content.

EXAMPLE 4

Multiple Materials

Using the bag configured as noted in Example 1, one can determine the effects of the addition of multiple materials. For example, a 5 cm$^2$ silicone gasket positioned on the 1 liter deuterated HDPE bag (described in Example 1 (for $^3$He)) with a starting $T_1$ of 132 hours will reduce the container's associated relaxation time. As pointed out in Equations 2.5, 2.6, relaxation rates are additive. Thus, to properly determine the container or equipment relaxation time, the relaxivities and corresponding surface areas of all the materials adjacent the free volume should be evaluated. The hypothetical silicone gasket, with an exemplary area "A" of 5 cm$^2$, the measured relaxivity of 0.0386 cm/min (p. 47, table 4.3), and free volume still at 1000 cc, gives a relaxation rate of about $1.9 \times 10^{-4}$/min. Adding the rate due to the bag itself ($1.3 \times 10^{-4}$/min) yields a total rate of about $3.2 \times 10^{-4}$/min which is inverted to get a $T_1$ of about 52 hours. Therefore, it is apparent that adding a very small surface area of a poor material can drastically shorten the $T_1$ despite the fact that most of the container material is good. Indeed, many commercially used O-ring materials can have relaxivities an order of magnitude higher than the one described, making the situation even worse. Thus, it is important to use substantially pure (impurity free) materials. The relaxivity for an available "off the shelf" silicone O-ring for $^{129}$Xe was measured at about 0.2–0.3 cm/min. For example, using the measured $^{129}$Xe relaxivity numbers for the $^3$He deuterated HDPE container will reduce the 132 hour bag down to just 15 hours (a full order of magnitude deterioration). The key is that every gasket, coupling, valve, tubing or other component that is added to the bag or container (especially those that are in fluid communication with the hyperpolarized gas) is preferably made of the friendliest possible material relative to the hyperpolarized state.

EXAMPLE 5

Measurement of Specific Material Properties

Measurement of specific material properties such as the relaxivities of materials is described above. For example, as noted in equation 2.5, relaxation rates attributed to various relaxation mechanisms are additive. Therefore, in order to measure the specific material property, a spin-down chamber such as that described herein can be used to determine two relaxation times for a hyperpolarized gas. Using the chamber consisting of two hemispheres sealed with an O-ring, the chamber is closed, HP ("hyperpolarized gas") is introduced therein, and the relaxation time $T_1$ is measured. Then the chamber is opened, a sample of known surface area is inserted, and the process is repeated to measure a new $T_1$. The new $T_1$ will be less than the old because a new relaxing surface has been added while keeping the free volume roughly the same. The difference between the two relaxation times is attributed to the relaxivity of the added material specimen. Thus, the difference can be used to calculate the material relaxivity using equation (2.10).

EXAMPLE 6

Validation of the Sorption Model

FIGS. 4.1 and 4.2 show the calculated and experimental $T_1$ values for $^{129}$Xe and $^3$He, respectively, in a 1 cc sphere for different surface materials as plotted against the product of solubility (S) and the square root of the molar density of protons in the material matrix $[1H]^{0.5}$. The 1 cc sphere value incorporates both volume and surface area and is a useful $T_1$ metric corresponding to conventional evaluations, and as such is typically more readily descriptive than the relaxivity parameters described herein. The $T_1$ value according to equation (2.23c) depends on a number of fixed constants and then depends inversely on gas solubility and the square root of the proton concentration. Experimental values of the measured one cubic centimeter sphere $T_1$ ($T_1^{cc}$) for all the polymers are plotted as well and show substantial agreement between theory and experiment, thus validating the sorption model described herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for storing, transporting, and delivering hyperpolarized gas to a target, comprising the steps of:
   hyperpolarizing a quantity of noble gas with spin exchange with an alkali metal;
   introducing a quantity of hyperpolarized gas into an expandable multi-layer container having opposing walls defined by multiple layers of materials, wherein the multiple layers of the container walls are securely attached together such that they are concurrently responsive to the application of pressure thereon, and wherein one of said layers is formed of a material resistant to the migration of oxygen into the container, and also wherein the hyperpolarized gas is processed such that it is non-toxic and substantially free of alkali metal and thereby suitable for in vivo administration;
   sealing the container to retain the hyperpolarized gas therein;
   transporting the container to a site remote from the hyperpolarization site; and
   compressing the container to collapse the chamber and force the hyperpolarized gas to exit therefrom, thereby delivering the hyperpolarized gas to a target.

2. A method according to claim 1, further comprising the step of inhibiting a major portion of the gas held in the container from flowing toward the port opening in the container during storage and transport.

3. A method according to claim 2, wherein said inhibiting step is performed by disposing a capillary flow passage in communication with the port of the container.

4. A method according to claim 2, wherein said inhibiting step is performed by substantially isolating a minor portion of the container from the main volume of the container.

5. A method according to claim 4, wherein said isolating step is performed by forcing a portion of the opposing walls of the container together.

6. A method according to claim 5, wherein said isolating step is performed by folding the minor portion of the container toward the main volume of the container to pinch together the opposing wall segments therebetween.

7. A method according to claim 1, wherein said hyperpolarized gas is $^3$He, and wherein the container includes one layer defining a gas contacting surface which is configured to inhibit the depolarizing contact-induced interaction of the hyperpolarized gas such that the hyperpolarized gas has a relaxation time longer than about 6 hours.

8. A method according to claim 1, wherein the walls include a hyperpolarized gas contacting surface formed by one of the multiple material layers, and wherein the gas contacting surface comprises a high purity metal which is substantially free of ferrous and paramagnetic impurities.

9. A method according to claim 1, wherein the walls include a hyperpolarized gas contacting surface formed by one of the multiple material layers wherein the gas contacting surface is formed by a layer comprising a polymer, and wherein a different layer of the multiple material layers forming the walls comprises a metal configured to define an oxygen shield overlying the layer forming the gas contacting surface.

10. A method according to claim 1, further comprising the step of configuring the container to inhibit the migration of oxygen into said chamber.

11. A method according to claim 1, wherein said filling step and said delivering step are repeated.

12. A method according to claim 1, wherein the target is a patient inhalation mask.

13. A method according to claim 1, wherein the hyperpolarized gas comprises $^{129}$Xe, and wherein the $T_1$ for the hyperpolarized gas held in the container resulting from one or more of contact-induced polarization loss and oxygen migration into said chamber is greater than about 6 hours.

14. A method according to claim 1, wherein the hyperpolarized gas comprises $^3$He, and wherein the $T_1$ for the hyperpolarized gas held in the container resulting from one or more of contact-induced polarization loss and oxygen migration into said chamber is greater than about 8 hours.

15. A method according to claim 1, wherein the inner layer of the multi-layer container is defined by a first material layer with a first thickness and the outer layer of the container is defined by a second material layer with a second thickness, the second material layer being configured to overlay and be secured to the first material layer, and wherein the second material is different from the first material.

16. A method according to claim 15, wherein the first material thickness is greater than the polarization decay length scale which is determined by the equation:

$$L_p = \sqrt{T_p D_p}$$

wherein $L_p$ is the polarization decay scale length, $T_p$ is the relaxation time of the noble gas in said first material, and $D_p$ is the noble gas diffusion coefficient in said first material.

17. A method according to claim 15, wherein said multi-layer container further comprises a third material layer overlaying and secured to said second material layer opposing said first material layer.

18. A method according to claim 17, wherein said multi-layer container further comprises a fourth material layer overlaying and secured to said third material layer opposing said second material layer.

19. A method according to claim 18, wherein said one of said second and third material layers is formed of an oxygen-shielding material, and wherein said first, second, and third material layers are formed of resilient materials such that said chamber has a first collapsed position and a second inflated position, corresponding respectively, to the container being void or filled.

20. A method according to claim 1, wherein the multi-layer container is configured to provide an oxygen permeability rate of less than about $1 \times 10^{-7}$ amgt/min when measured at one atmosphere of pressure.

21. A method according to claim 1, wherein one of the layers of the multi-layer container comprises a high purity metal which is substantially free of ferrous and paramagnetic impurities.

22. A method according to claim 20, wherein at least one of said second and third material layers comprises a metal film configured to overlay the adjacently disposed layer.

23. A method according to claim 1, wherein at least one of the layers of the multi-layer container comprises a material chosen from the group consisting of polyolefin, polystyrene, polymethacrylate, polyvinyl, polydiene, polyester, polycarbonate, polyamide, polyimide, polynitriles, cellulose and cellulose derivatives, and blends and mixtures thereof.

24. A method according to claim 1, wherein at least one of the layers of the multi-layer container comprises a material chosen from the group consisting of high-density polyethylene, low-density polyethylene, polypropylene having about 50% crystallinity, polyvinylfluoride, polyamide, polyimide, polynitriles, and cellulose, and blends and mixtures thereof.

25. A method according to claim 1, wherein said hyperpolarized gas comprises $^3$He, and wherein the multi-layer container comprises an inner surface material with a relaxivity value of less than about 0.0013 cm/min.

26. A container according to claim 1, wherein said hyperpolarized gas comprises $^{129}$Xe, and wherein the multi-layer container comprises an inner surface material with a relaxivity value of less than about 0.012 cm/min.

27. A method for preparing an expandable storage container for receiving a quantity of hyperpolarized gas, comprising the steps of:

providing a quantity of purge gas into the hyperpolarized gas expandable container;

expanding the hyperpolarized gas container by directing a quantity of purge gas therein;

collapsing the hyperpolarized gas container by removing purge gas therefrom;

outgassing the oxygen in the container walls by decreasing the oxygen partial pressure in the container thereby causing a substantial amount of the oxygen trapped in the walls of the container to migrate into the chamber of the container in the gas phase;

filling a container with a quantity of storage gas after said outgassing step to a pressure which reduces the pressure differential across the walls of the container to reduce further outgassing of the container;

storing the container for future use; and then removing the storage gas and outgassed oxygen from the container before filling with a quantity of hyperpolarized gas.

28. A method according to claim 27, wherein the purge gas comprises nitrogen.

29. A method according to claim 28, wherein the expandable container comprises a wall that is configured as a unitary polymer material layer with a thickness which provides an oxygen permeability rate at one atm of less than about $1 \times 10^{-7}$ amgt/min.

30. A method according to claim 27, wherein the storage gas comprises nitrogen.

31. A method according to claim 27, wherein the expandable container is formed of multiple layers of material that are concurrently responsive to pressure.

32. A method according to claim 27, wherein the hyperpolarized gas comprises $^3$He.

33. A method according to claim 27, wherein the hyperpolarized gas comprises $^{129}$Xe.

* * * * *